United States Patent
Kawaguchi et al.

(10) Patent No.: US 9,480,417 B2
(45) Date of Patent: Nov. 1, 2016

(54) POSTURE ESTIMATION DEVICE, POSTURE ESTIMATION SYSTEM, AND POSTURE ESTIMATION METHOD

(75) Inventors: Kyoko Kawaguchi, Tokyo (JP); Masamoto Tanabiki, Kanagawa (JP); Kensuke Maruya, Osaka (JP); Yuji Sato, Tokyo (JP); Mitsuko Fujita, Tokyo (JP)

(73) Assignee: PANASONIC CORPORATION, Osaka (JP)

( * ) Notice: Subject to any disclaimer, the term of this patent is extended or adjusted under 35 U.S.C. 154(b) by 170 days.

(21) Appl. No.: 13/819,784
(22) PCT Filed: Feb. 20, 2012
(86) PCT No.: PCT/JP2012/001113
§ 371 (c)(1),
(2), (4) Date: Apr. 15, 2013
(87) PCT Pub. No.: WO2012/117687
PCT Pub. Date: Sep. 7, 2012

(65) Prior Publication Data
US 2014/0163424 A1 Jun. 12, 2014

(30) Foreign Application Priority Data
Mar. 2, 2011 (JP) ................................ 2011-045012

(51) Int. Cl.
A61B 5/11 (2006.01)
G06T 7/00 (2006.01)
A61B 5/00 (2006.01)

(52) U.S. Cl.
CPC .......... *A61B 5/1128* (2013.01); *A61B 5/0077* (2013.01); *A61B 5/1116* (2013.01); *A61B 5/7207* (2013.01); *G06T 7/0044* (2013.01); *G06T 2207/30196* (2013.01)

(58) Field of Classification Search
CPC ..... A61B 5/11; A61B 5/1116; A61B 5/4528; A61B 5/1128; A61B 5/7203; G06K 9/00362; G06K 9/00369; G06K 9/00375; G06K 9/00382; G06K 9/00389; G06K 9/00395; Y10S 128/92; Y10S 128/922; Y10S 128/923; Y10S 128/924; G06T 7/0044; G06T 2207/30196
USPC ........ 600/300, 301, 587, 595; 382/103, 190, 382/195, 199, 203, 209, 216; 128/922–924; 348/154, 155; 700/259
See application file for complete search history.

(56) References Cited

U.S. PATENT DOCUMENTS 6,557,010 B1 4/2003 Kim et al.
7,424,174 B2 9/2008 Furuhashi et al.
(Continued)

FOREIGN PATENT DOCUMENTS

CN 1820282 A 8/2006
CN 1950844 A 4/2007
(Continued)

OTHER PUBLICATIONS

Bissacco, et al, "Fast Human Pose Estimation using Appearance and Motion via Multi-Dimensional Boosting Regression," Computer Vision and Pattern Recognition, 2007. CVPR '07. IEEE Conference on , vol., no., pp. 1,8, Jun. 17-22, 2007. Retreived from <http://ieeexplore.ieee.org/stamp/stamp.jsp?tp=&arnumber=4270154&isnumber=4269956> on Dec. 4, 2014.*
Cucchiara, et al, "Probabilistic posture classification for Human-behavior analysis," Systems, Man and Cybernetics, Part A: Systems and Humans, IEEE Transactions on , vol. 35, No. 1, pp. 42,54, Jan. 2005. Retreived from <http://ieeexplore.ieee.org/stamp/stamp.jsp?tp=&arnumber=1369344&isnumber=29969> on Dec. 4, 2014.*
(Continued)

*Primary Examiner* — Devin Henson
*Assistant Examiner* — David J McCrosky
(74) *Attorney, Agent, or Firm* — Pearne & Gordon LLP

(57) ABSTRACT

Provided is a posture estimation device with which it is possible to estimate the posture of an object having joints with a high degree of precision. A posture estimation device (100) carries out an estimation of a posture of an object on the basis of image data. An object having a plurality of sites which are connected by joints is photographed. The posture estimation device includes a reference model storage unit (140) which stores a reference model, which defines the locations of the sites, for each posture. A weighting computation unit (150) carries out weighting on the sites for each posture such that the weighting of concentrated parts is reduced. A posture estimation unit (160) estimates the posture of the object by applying the weighting and comparing the reference model with the object.

7 Claims, 25 Drawing Sheets

(56) References Cited

U.S. PATENT DOCUMENTS

| | | | |
|---|---|---|---|
| 7,706,601 B2* | 4/2010 | Hamanaka | 382/154 |
| 7,986,813 B2 | 7/2011 | Hamanaka | |
| 8,073,201 B2 | 12/2011 | Satoh et al. | |
| 2006/0098865 A1 | 5/2006 | Yang et al. | |
| 2006/0120606 A1 | 6/2006 | Furuhashi et al. | |
| 2007/0078564 A1 | 4/2007 | Hoshino et al. | |
| 2007/0268295 A1 | 11/2007 | Okada | |
| 2007/0269080 A1 | 11/2007 | Hamanaka | |
| 2009/0022369 A1 | 1/2009 | Satoh et al. | |
| 2009/0080780 A1* | 3/2009 | Ikeda | 382/209 |
| 2010/0111370 A1* | 5/2010 | Black et al. | 382/111 |
| 2010/0188519 A1* | 7/2010 | Yamaoka et al. | 348/222.1 |
| 2011/0172927 A1* | 7/2011 | Sahasrabudhe et al. | 702/19 |

FOREIGN PATENT DOCUMENTS

| | | |
|---|---|---|
| CN | 101116101 A | 1/2008 |
| JP | 2001-134615 A | 5/2001 |
| JP | 2005-351814 A | 12/2005 |
| JP | 2007-310707 A | 11/2007 |
| JP | 2008-519357 A | 6/2008 |
| WO | 2005/046942 A1 | 5/2005 |

OTHER PUBLICATIONS

"Relative", The American Heritage Dictionary of the English Language, Fifth Edition (2014), Houghton Mifflin Harcourt Publishing Company. Retrieved from <https://ahdictionary.com/word/search.html?q=relative> on Apr. 20, 2015.*

Ryuzo Okada et al; Human Posture Estimation using Silhouette-Tree-Based Filtering; Meeting on Image Recognition and Recognition and Understanding (MIRU 2006); Jul. 2006; pp. 63-69.

Masamichi Shimosaka et al; Motion Recognition Using Shape Features in Monocular Images; In the collection of presentation papers from the 70th National Convention in 2008 (5); Information Processing Society of Japan; Mar. 13, 2008; pp. 5-93 & 5-94.

Paul Viola et al; Rapid Object Detection Using a Boosted Cascade of Simple Features; In Proc. of CVPR; vol. 1; Dec. 2001; pp. 511-518.

International Search Report for PCT/JP2012/00113 dated Mar. 13, 2012.

English Translation of Search Report for Chinese Patent Application No. 201280002019.9 dated Feb. 3, 2015.

* cited by examiner

| IDENTIFIER | PROJECTION ANGLE | COORDINATES OF LEFT SHOULDER POSITION | COORDINATES OF GEOMETRIC CENTER POSITION OF HEAD | ORIENTATION OF REFERENCE PARTS (DEGREES) |
|---|---|---|---|---|
| 1 | 45 | 1, 0 | $0.5, \dfrac{1}{2\sqrt{3}}$ | 0, 0, 0 |
| 2 | 45 | $\dfrac{1}{\sqrt{2}}, -\dfrac{1}{\sqrt{2}}$ | 0.3, 1.2 | 0, 45, 0 |
| ... | ... | ... | ... | ... |

FIG. 20

| IDENTIFIER | PROJECTION ANGLE | HEAD-SHOULDER REGION POSITION (RIGHT SHOULDER POSITION IN IMAGE) | HEAD-SHOULDER REGION ORIENTATION (ANGLE) | RIGHT UPPER ARM (CENTER COORDINATES AND RADIUS) | LEFT UPPER ARM (CENTER COORDINATES AND RADIUS) | ... |
|---|---|---|---|---|---|---|
| 1 | 45 | 300, 250 | 0, 0, 0 | 300, 250, 100 | 350, 250, 100 | ... |
| 2 | 45 | 300, 250 | 0, 45, 0 | ... | ... | ... |
| ... | ... | ... | ... | ... | ... | ... |

FIG. 21

POSTURE ESTIMATION DEVICE, POSTURE ESTIMATION SYSTEM, AND POSTURE ESTIMATION METHOD

TECHNICAL FIELD

The claimed invention relates to a posture estimation apparatus, posture estimation system, and posture estimation method that estimate the posture of an object based on image data capturing the object, the object having a plurality of parts articulated by one or more joints.

BACKGROUND ART

Human posture estimation based on image data from a captured video sequence has been an active area of research in recent years. This is because being able to determine human behavior based on videos through computer analysis would make behavior analysis, which is performed in various fields, possible without requiring human effort. Examples of behavior analysis include abnormal behavior detection on the streets, purchasing behavior analysis in stores, factory streamlining support, and form coaching in sports.

In this respect, PL 1 and NPL 1, for example, disclose a technique for estimating the posture of a person based on image data captured with a monocular camera.

In the technique disclosed in PL 1 and NPL 1 (hereinafter referred to as "the related art technique"), a silhouette of a model image (a model silhouette) is prepared on a per posture basis. The related art technique then estimates that the posture of the silhouette that is most similar to the silhouette extracted from the captured image (observation target silhouette) is the posture of the subject included in the captured image. Specifically, the related art technique computes a silhouette distance based on the per-pixel exclusive or's of the model silhouette and the observed silhouette, and determines the degree of similarity to be high if the silhouette distance is small.

However, even for the same posture, the outline portion of a silhouette may vary significantly in terms of position and angle. As such, in computing silhouette distances, the related art technique assigns greater weights to the logical or's of the pixels in accordance with how close the pixels are to the center of the observed silhouette. Thus, the related art technique enables posture estimation that is robust against noise (variability) in the outline portion.

CITATION LIST

Patent Literature

PTL 1
Japanese Patent Application Laid-Open No. 2007-310707

Non-Patent Literature

NPL 1
Ryuzo OKADA and Björn STENGER, "Human Posture Estimation using Silhouette-Tree-Based Filtering," Meeting on Image Recognition and Understanding (MIRU 2006), July 2006, pp. 63-69

NPL 2
Masamichi Shimosaka, Makoto Sato, Taketoshi Mori, and Tomomasa Sato, "Motion Recognition Using Shape Features in Monocular Images," in the collection of presentation papers from the $70^{th}$ National Convention in 2008 (5), Information Processing Society of Japan, Mar. 13, 2008, p. 5-93, p. 5-94

NPL 3
P. Viola and M. Jones, "Rapid Object Detection Using a Boosted Cascade of Simple Features," in Proc. of CVPR, vol. 1, December, 2001, ppp. 511-518

SUMMARY OF INVENTION

Technical Problem

However, the related art technique has a problem in that certain postures cannot be estimated accurately. This is because, while the related art technique does assign weights for each part based on the distance from the center position of the part, it fails to make effective use of characteristic posture information. By way of example, whereas the forearm provides characteristic posture information with regard to a posture where the arm is extended, it does not with regard to a posture where the arm is dangling. However, comparable weights are assigned to the forearm in those postures.

Furthermore, while the related art technique could be applied to various objects, besides humans, having a plurality of parts articulated by joints (e.g., robots), similar problems could still arise in such cases.

An object of the claimed invention is to provide a posture estimation apparatus, posture estimation system, and posture estimation method that are capable of accurately estimating the posture of an object having one or more joints.

Solution to Problem

A posture estimation apparatus of the claimed invention includes a posture estimation apparatus that estimates the posture of an object including a plurality of parts articulated by one or more joints based on image data that images the object, the posture estimation apparatus including: a reference model storage section that stores, on a per posture basis, a reference model defining positions of the parts; a weight computation section that weights, on a per posture basis, the parts in such a manner as to assign a lesser weight to a crowded area; and a posture estimation section that estimates the posture of the object by comparing the reference model and the object while using the weights.

A posture estimation system of the claimed invention includes a posture estimation system including: a posture estimation apparatus that estimates the posture of an object including a plurality of parts articulated by one or more joints based on image data that images the object; and a weight determination apparatus including: a first reference model storage section that stores, on a per posture basis, a reference model defining positions of the parts; a weight computation section that weights, on a per posture basis, the parts in such a manner as to assign a lesser weight to a crowded area; and a weight information storage section that stores weight information indicating the weights, wherein the posture estimation apparatus includes: a second reference model storage section that stores the reference model; a weight information acquisition section that obtains the weight information from the weight determination apparatus; and a posture estimation section that estimates the posture of the object by comparing the reference model and the object while using the obtained weight information.

A posture estimation method of the claimed invention includes a posture estimation method that estimates the posture of an object including a plurality of parts articulated by one or more joints based on image data that images the object and using a reference model that defines positions of the parts on a per posture basis, the posture estimation method including the steps of: weighting, on a per posture basis, the parts in such a manner as to assign a lesser weight to a crowded area; and estimating the posture of the object by comparing the reference model and the object while using the weights.

Advantageous Effects of Invention

With the claimed invention, the posture of an object having one or more joints may be estimated accurately.

BRIEF DESCRIPTION OF DRAWINGS

FIG. 20 is a diagram showing example contents of a reference part correspondence table with respect to Embodiment 3;

FIG. 21 is a diagram showing example contents of a part region correspondence table with respect to Embodiment 3;

DESCRIPTION OF EMBODIMENTS

Figure 1:
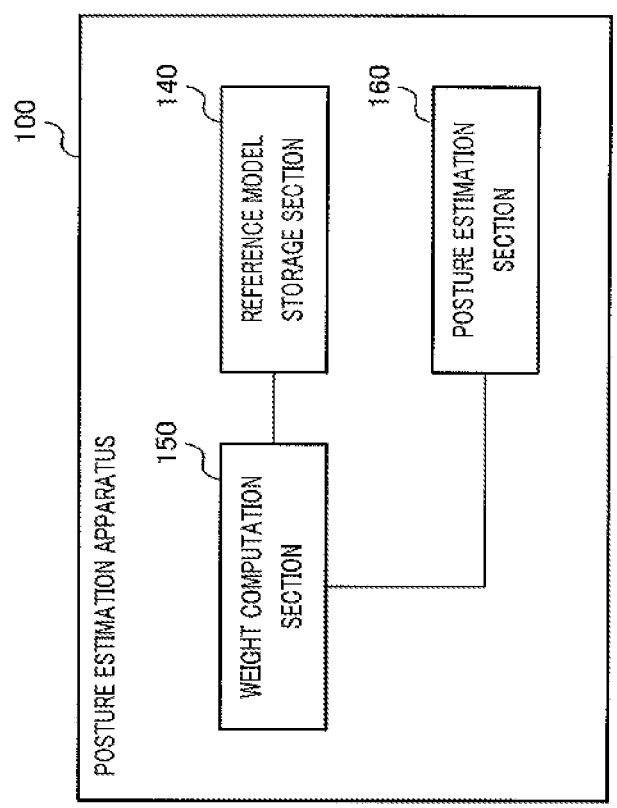
FIG. 1 is a block diagram showing a configuration example of a posture estimation apparatus according to Embodiment 1 of the claimed invention.

Embodiments of the claimed invention are described in detail below with reference to the drawings. Embodiment 1 and Embodiment 2 of the claimed invention are basic embodiment examples of the claimed invention. Embodiment 3 of the claimed invention includes specific embodiment examples of the claimed invention.

In the context of the embodiments described below, the term "part" refers to one unit among portions of the human anatomy divided by joints. In other words, the term part may refer to, for example, the head, the shoulders, the right upper arm, the right forearm, the left upper arm, the left forearm, the right thigh, the right crus, the left thigh, or the left crus. Further, the term "part region" refers to a region that could be occupied by a given part within an image, i.e., the range of motion of a part.

The term "part count" refers to the total number of parts that are subject to evaluation in relation to posture estimation. Specifically, for example, if posture estimation is to be performed with the whole body being subject to evaluation, the part count would be the number of parts as categorized into the head, the shoulders (including the torso), the right upper arm, the right forearm, the left upper arm, the left forearm, the right thigh, the right crus, the left thigh, and the left crus. Thus, the part count would be "10".

In addition, the term "part axis" refers to an imaginary center axis that runs through the length of a given part. Specifically, the term part axis refers to a line segment that connects a first joint, which articulates a given part with a first other part on the reference part side, and a second joint, or the end portion of the given part, that articulates the given part with a second other part. A part axis may be defined through a combination of coordinate information for the first joint, angle information, and part length, for example. It may also be defined through coordinate information for the first joint and coordinate information for the second joint or the end portion of the given part. By way of example, the position, orientation, and length of the part axis of the right upper arm generally coincide with the position, orientation, and length of the center axis of the bone of the right upper arm.

The term "part thickness" refers to the thickness of a part around the part axis, which may be, for example, its on-screen width.

The term "part candidate" refers to a candidate for the position of a part, which is the position of the part as estimated from image data.

The term "silhouette" refers to a candidate for an enclosed region occupied by the body of one person on the screen, which is the position of the body as estimated from an image. Where appropriate, part candidates and silhouette candidates may be referred to collectively as "body candidates."

"Posture" may be represented by such information as the position of a joint articulating parts in a two-dimensional coordinate system or three-dimensional coordinate system, the lengths of the parts concerned, the angle formed between parts, and the like. Accordingly, the term "posture estimation" involves estimating a posture by estimating such information. The positions, lengths, and angles mentioned above may be expressed through relative values that reference a predetermined human body part, or through absolute values in a two-dimensional coordinate system or three-dimensional coordinate system.

Although descriptions are provided using pixels as basic units of processing for the various embodiments below, a posture estimation apparatus may also perform similar processes by treating a group of pixels of a predetermined size as one pixel. This would enable a posture estimation apparatus to carry out high-speed processing. When treating a plurality of pixels as one pixel, the value of the pixel that is the geometric center of the plurality of pixels may be used as the value of those plurality of pixels, or the average value of the values of the plurality of pixels may be used as the value of those plurality of pixels.

(Embodiment 1)

FIG. 1 is a block diagram showing the configuration of a posture estimation apparatus according to an embodiment of the claimed invention.

With respect to FIG. 1, posture estimation apparatus 100 according to an embodiment of the claimed invention is an apparatus that estimates the posture of a person, which is an object including a plurality of parts articulated by joints, based on image data of that person. Posture estimation apparatus 100 includes: reference model storage section 140; weight computation section 150; and posture estimation section 160.

Reference model storage section 140 stores, on a per posture basis, a reference model defining part positions.

Weight computation section 150 weights, on a per posture basis, parts in such a manner as to assign lesser weights to crowded areas. The term "crowded area" as used above refers to an area where a plurality of parts are densely located, as in the various parts of both arms when they are folded in front of the torso, and so forth. In other words, crowded areas are susceptible to noise during posture estimation.

By comparing reference models and a person while using the above-mentioned weights, posture estimation section 160 estimates the posture of a person.

Posture estimation apparatus 100 includes, for example: a central processing unit (CPU); a storage medium (e.g., read-only memory (ROM)) storing a control program; and working memory (e.g., random-access memory (RAM)). In this case, the functions of the various parts mentioned above are realized by having a control program executed by the CPU.

This posture estimation apparatus 100 is able to perform posture estimation with the influence of the crowded area, where noise tends to occur, reduced. Furthermore, posture estimation apparatus 100 is thus able assign relatively greater weights to parts that are far apart from other parts and serve as feature areas for a given posture (hereinafter referred to as "dispersed areas"), e.g., the hands and forearms of arms that are spread outward. Accordingly, since posture estimation apparatus 100 assigns weights corresponding to the level of influence that each part has on posture estimation accuracy, it is possible to accurately estimate the posture of a human having joints.

A description has been provided above with respect to an example where weight computation section 150 weights, on a per posture basis, parts in such a manner as to assign lesser weights to crowded areas. However, the weights assigned to dispersed areas may be increased instead so that the weights assigned to crowded areas become relatively smaller.

(Embodiment 2)

Figure 2:
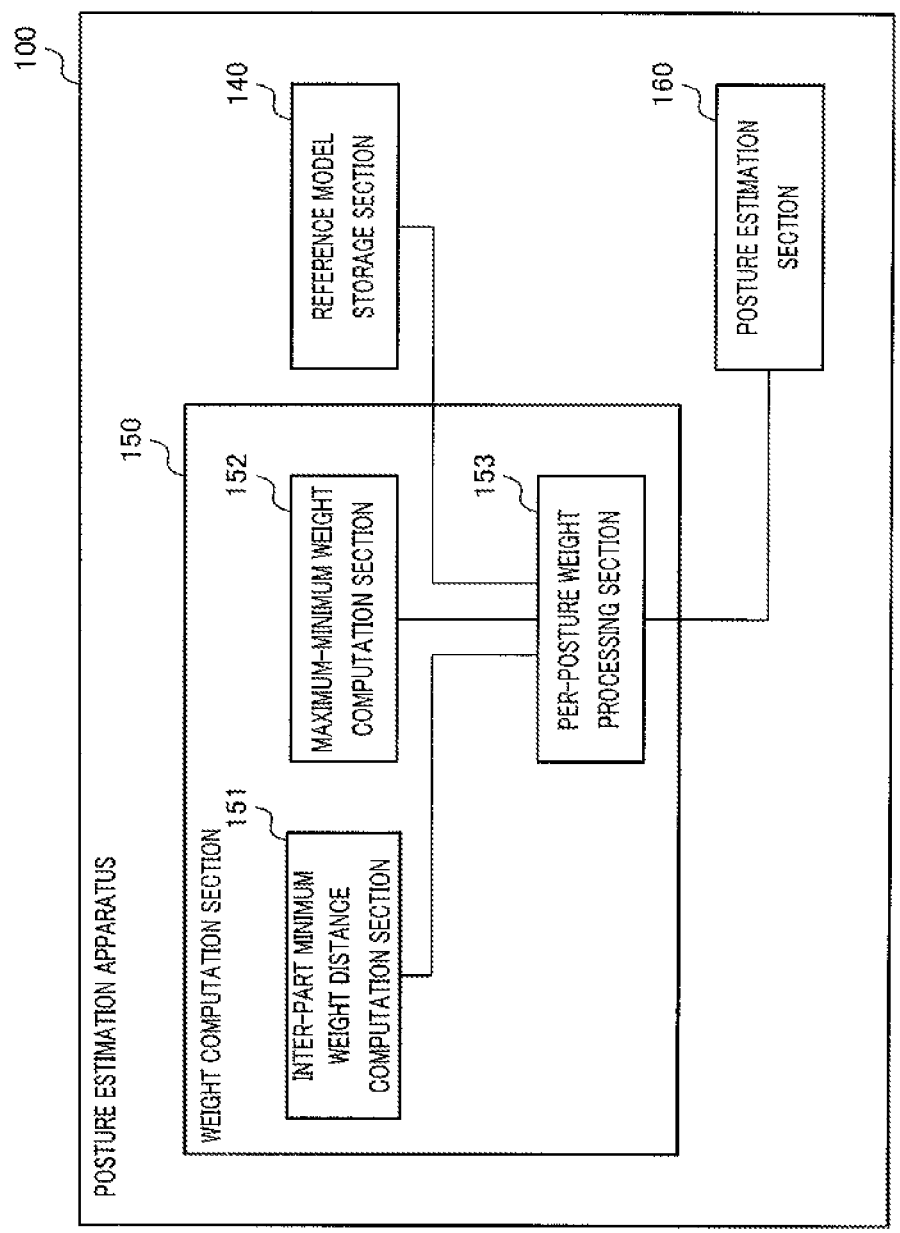
FIG. 2 is a block diagram showing a configuration example of a posture estimation apparatus according to Embodiment 2 of the claimed invention.

FIG. 2 is a block diagram showing the configuration of a posture estimation apparatus according to an embodiment of the claimed invention.

With respect to FIG. 2, posture estimation apparatus 100 according to an embodiment of the claimed invention is an apparatus that estimates the posture of a person, which is an object including a plurality of parts articulated by joints, based on image data for that person. Posture estimation apparatus 100 includes: reference model storage section 140; weight computation section 150; and posture estimation section 160.

Reference model storage section 140 stores, on a per posture basis, a reference model defining part positions.

Weight computation section 150 weights, on a per posture basis, parts in such a manner as to assign lesser weights to crowded areas. Weight computation section 150 includes; inter-part minimum weight distance computation section 151; maximum-minimum weight computation section 152; and per-posture weight processing section 153.

For each part, inter-part minimum weight distance computation section 151 computes an inter-part minimum weight distance. Inter-part minimum weight distance is a parameter that indicates a range where, when some other part is located thereat, the presence of this other part is likely to become the above-mentioned posture estimation noise.

Maximum-minimum weight computation section 152 holds weight ranges.

For each posture, per-posture weight processing section 153 determines a small weight or a large weight for each part of a reference model and within the above-mentioned weight ranges, and thus determines a weight for each part of the reference model. More specifically, of the parts of a reference model, per-posture weight processing section 153 determines small weights for parts for which other parts corresponding to their inter-part minimum weight distances are located within the ranges indicated by those inter-part minimum weight distances. On the other hand, per-posture weight processing section 153 determines large weights for parts for which other parts corresponding to their inter-part minimum weight distances are not located within the ranges indicated by those inter-part minimum weight distances.

By comparing a reference model and a person while using the weights determined by per-posture weight processing section 153, posture estimation section 160 estimates the posture of the person.

Posture estimation apparatus 100 includes, for example: a CPU; a storage medium (e.g., ROM) storing a control program; and working memory (e.g., RAM). In this case, the functions of the various parts mentioned above are realized by having a control program executed by the CPU.

This posture estimation apparatus 100 is able to treat a range, where, when some other part is located thereat, the presence of this other part is likely to become noise with respect to posture estimation, as a crowded area for which a small weight should be determined. Such a range is, in other words, an image region, and is a range indicated by an inter-part minimum weight distance. As posture estimation apparatus 100 is thus able to appropriately set small weights for parts that are susceptible to noise, it is capable of accurately estimating the posture of a human having joints.

(Embodiment 3)

Figure 3:
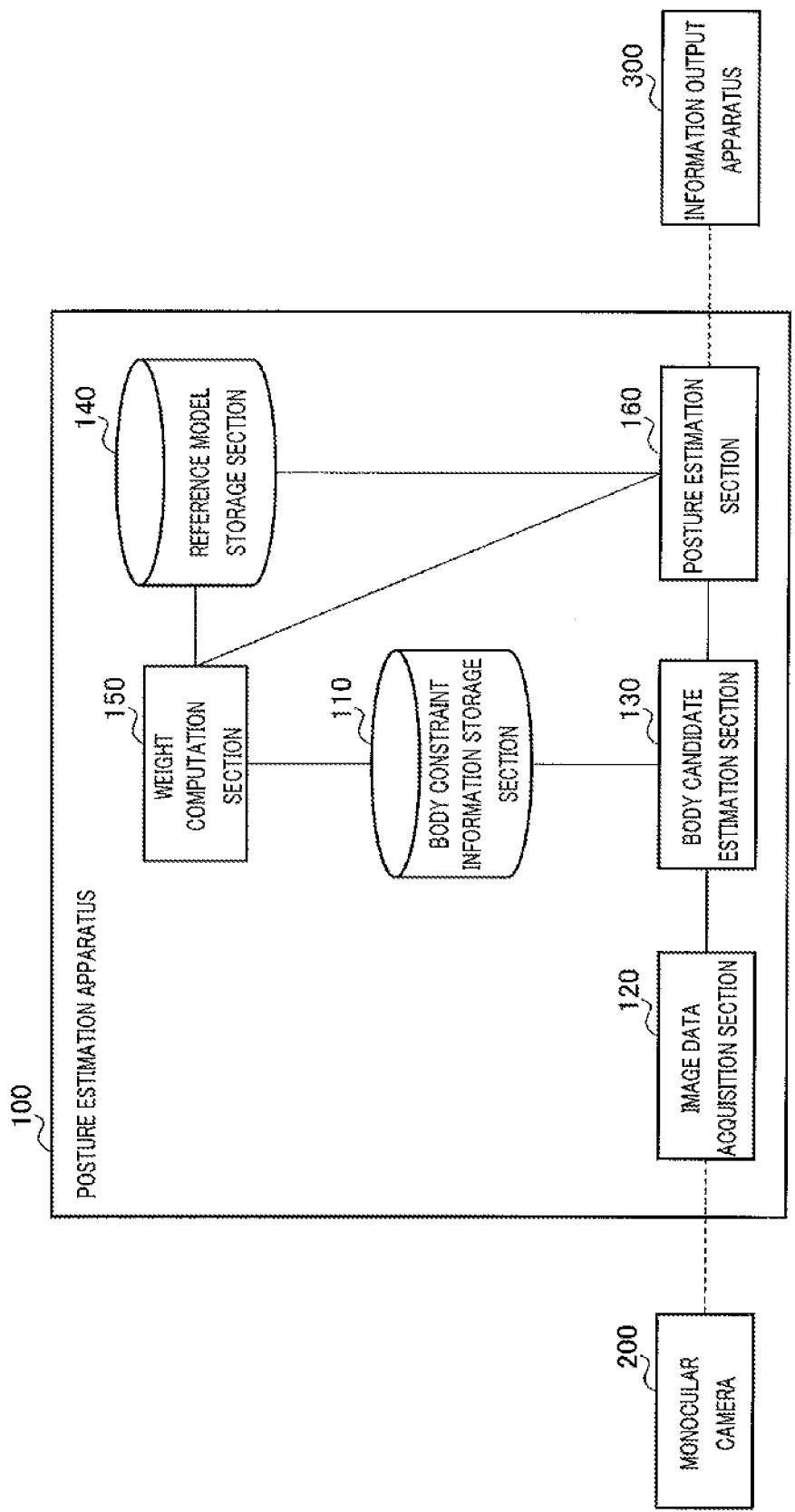
FIG. 3 is a block diagram showing a first configuration example of a posture estimation apparatus according to Embodiment 3 of the claimed invention.

FIG. 3 is a block diagram showing the configuration of a posture estimation apparatus according to an embodiment of the claimed invention. For purposes of convenience, peripheral devices of the posture estimation apparatus are also shown in the diagram.

With respect to FIG. 3, posture estimation apparatus 100 according to an embodiment of the claimed invention is an apparatus that estimates the posture of a person, which is an object including a plurality of parts articulated by joints, based on image data of that person. Posture estimation apparatus 100 includes: body constraint information storage section 110; image data acquisition section 120; body candidate estimation section 130; reference model storage section 140; weight computation section 150; and posture estimation section 160.

Body constraint information storage section 110 pre-stores constraint conditions regarding human anatomy and posture (hereinafter referred to as "body constraint information"). Body constraint information is information that is used for part region estimation and part candidate extraction, which are hereinafter discussed. The specifics of body constraint information vary depending on the part region estimation method and part candidate extraction method, and as such will be discussed later.

Image data acquisition section 120 obtains, by wire or wirelessly, image data of an image taken with monocular camera 200 installed in a predetermined three-dimensional coordinate space, and outputs it to body candidate estimation section 130. For the present embodiment, it is assumed that monocular camera 200 is a video camera. Image data acquisition section 120 receives video data captured continuously in real time by monocular camera 200 as input, and sequentially outputs to body candidate estimation section 130 still image data that forms the video data. In the following description, it is assumed that the image data contains images of one person only. However, this is by no means limiting, and it may contain images of a plurality of people, or of none at all.

Figure 4:
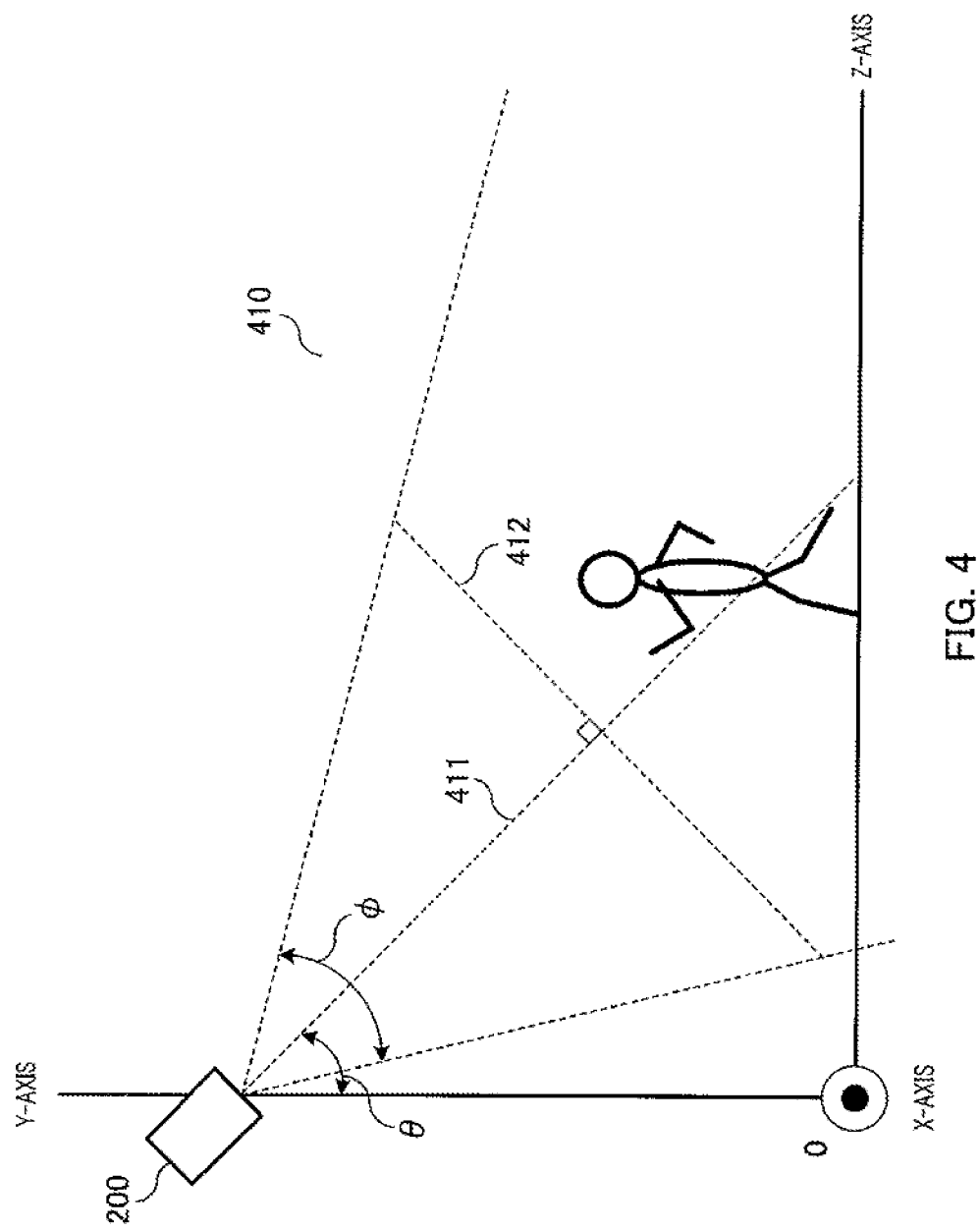
FIG. 4 is a diagram illustrating image data with respect to Embodiment 3.

FIG. 4 is a diagram illustrating image data.

Three-dimensional coordinate system 410 is set up as shown in FIG. 4, where the position of monocular camera 200 as projected onto the ground is taken to be origin O, for example. Coordinate system 410 takes the perpendicular direction to be the Y-axis, a direction orthogonal to the Y-axis and optical axis 411 of monocular camera 200 to be the X-axis, and a direction orthogonal to the X-axis and the Y-axis to be the Z-axis, for example.

The installation angle of monocular camera 200 is denoted by angle θ formed between the Y-axis and optical axis 411, for example. Monocular camera 200 performs imaging by focusing on plane 412 contained in the range within view angle φ of monocular camera 200. Image data of the image thus captured is sent to posture estimation apparatus 100.

Based on the image data received from image data acquisition section 120, body candidate estimation section 130 in FIG. 3 obtains a body candidate (a silhouette or a part candidate) for the person. Body candidate estimation section 130 then outputs, to posture estimation section 160, body candidate information (silhouette information or part candidate information) indicating the thus obtained body candidate. For the present embodiment, it is assumed that body candidate estimation section 130 obtains a part candidate for the person, and outputs part candidate information.

Figure 5:
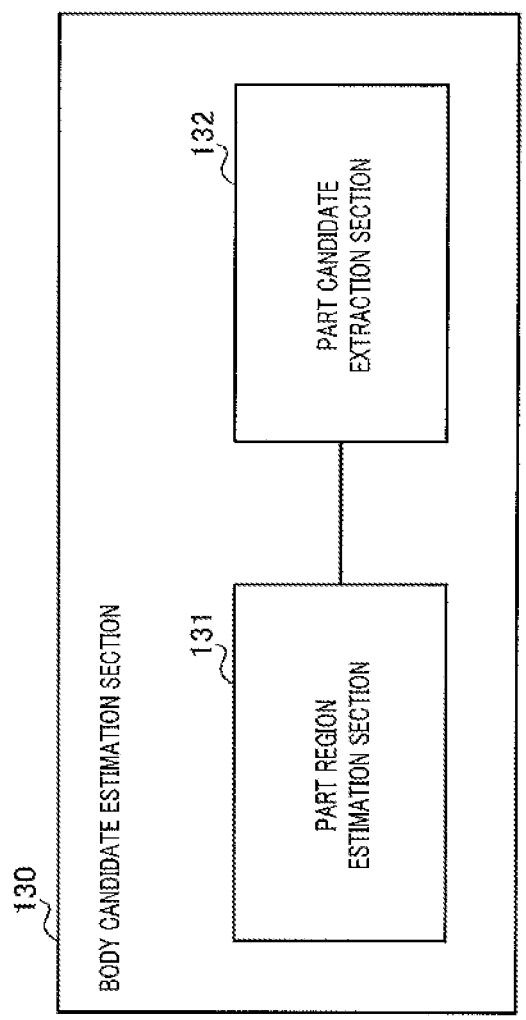
FIG. 5 is a block diagram showing a configuration example of a body candidate estimation section with respect to Embodiment 3.

FIG. 5 is a block diagram showing a configuration example of body candidate estimation section 130.

With respect to FIG. 5, body candidate estimation section 130 includes: part region estimation section 131; and part candidate extraction section 132.

Based on image data received from image data acquisition section 120, part region estimation section 131 estimates the part regions of various parts. Specifically, based on image data received from image data acquisition section 120, it estimates the part regions of various parts. Specifically, based on the image data, part region estimation section 131 estimates the positions and orientation of reference parts of a person. The "reference parts" are parts for which position and orientation estimation is performed before any other part, and whose estimation result bears on the position and orientation estimations of other parts. With the estimated positions and orientation of the reference parts as references, part region estimation section 131 estimates the part regions of various parts.

The reference parts should preferably be parts that allow stable image acquisition in the image acquisition space. As such, for the present embodiment, it is assumed that the reference parts include the head and shoulders of a person. It is assumed that the orientation of the reference parts is the orientation of the shoulders, where the orientation of the shoulders is defined as the direction of a straight line connecting the right shoulder and the left shoulder. Part region estimation section 131 outputs to part candidate extraction section 132 the image data and information indicating the part region of each part (hereinafter referred to as "part region data"). In the present embodiment, an image is obtained from above as shown in FIG. 4. Accordingly, taking the head and shoulders of a person to be the reference parts enables the most stable estimation.

Based on the received image data and the received part region data, part candidate extraction section 132 extracts part candidates. Part candidate extraction section 132 outputs to posture estimation section 160 the image data and part candidate information indicating the extracted part candidates. For the present embodiment, it is assumed that a part candidate is expressed in terms of a position in an image, that is, in terms of a two-dimensional coordinate system for the image. It is assumed that the part candidate information is a likelihood map indicating a distribution of likelihoods regarding the position of each part.

Specifically, in the present embodiment, part candidate extraction section 132 generates a likelihood map where, for regions other than the part regions indicated by the part region data received from part region estimation section 131, the likelihood that designated parts corresponding to those part regions are located thereat is set low. A likelihood map generated based on image data is hereinafter referred to as an "estimated likelihood map."

For each posture that could be returned as a posture estimation result by posture estimation section 160 in FIG. 3, reference model storage section 140 in FIG. 3 stores reference model two-dimensional information. Reference model two-dimensional information is information that represents a reference model in a given posture through relative positional relationships of various parts as projected onto a given two-dimensional plane. Reference model two-dimensional information may be numbered projected image information for each part, such as that disclosed in NPL 1, or information including the position and angle of each part. Reference model two-dimensional information will be discussed in detail later.

Weight computation section 150 shown in FIG. 3 references the body constraint information of body constraint information storage section 110, and determines, for each posture for which reference model two-dimensional information is stored in reference model storage section 140, a weight for each part of the reference model. More specifically, for each posture, weight computation section 150 weights the parts in such a manner as to assign lesser weights to crowded areas. Weight computation section 150 then outputs to posture estimation section 160 weight information indicating the thus determined weights.

Figure 6:
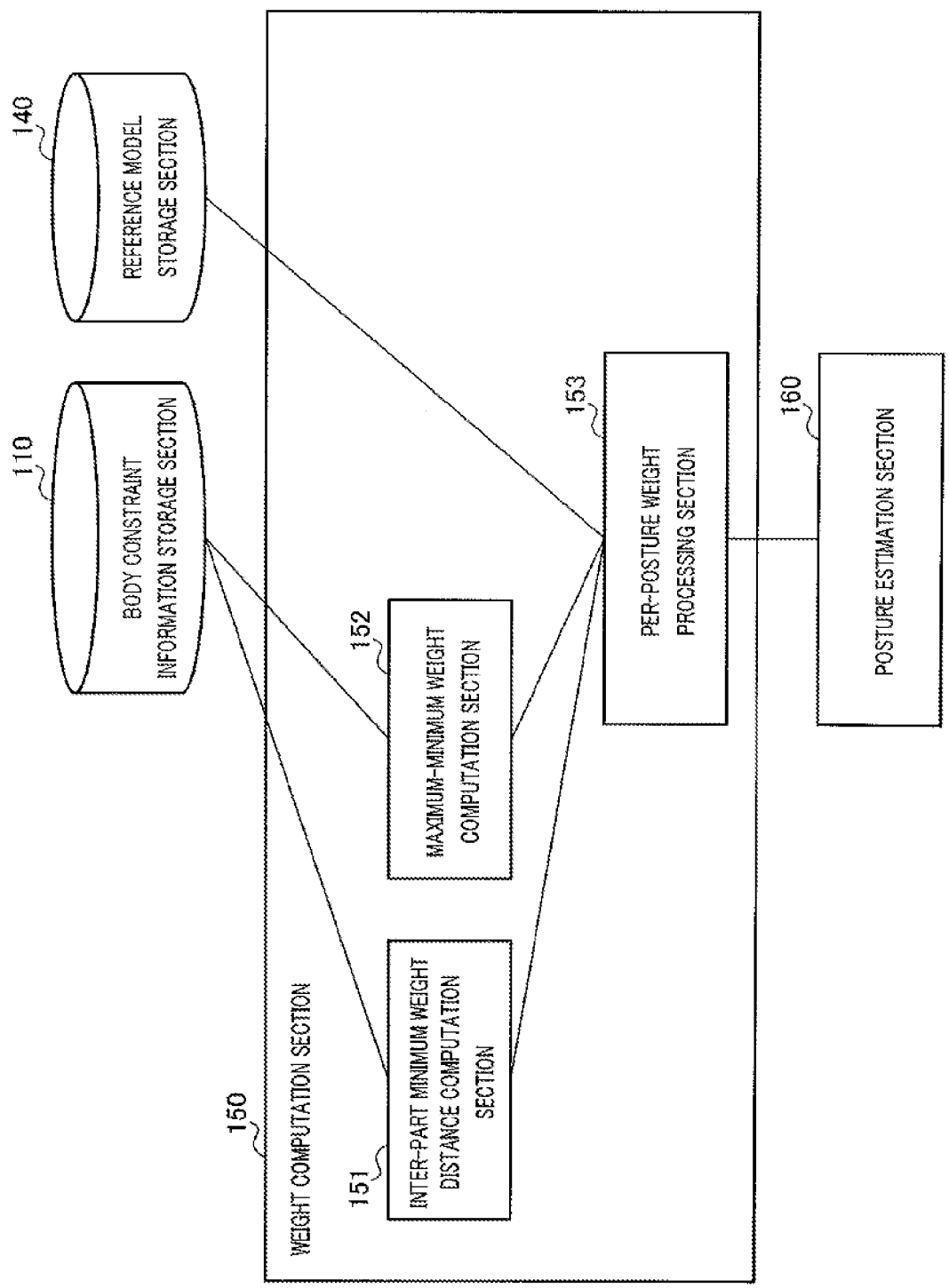
FIG. 6 is a block diagram showing a configuration example of a weight computation section with respect to Embodiment 3.

FIG. 6 is a block diagram showing a configuration example of weight computation section 150. For purposes of convenience, functional sections peripheral to weight computation section 150 are also shown in the diagram.

With respect to FIG. 6, weight computation section 150 includes: inter-part minimum weight distance computation section 151; maximum-minimum weight computation section 152; and per-posture weight processing section 153.

Inter-part minimum weight distance computation section 151 references body constraint information storage section 110, and computes an inter-part minimum weight distance for each posture and each part of a reference model. As mentioned above, inter-part minimum weight distance is a parameter that indicates a range where, when some other part is located thereat, the presence of this other part is likely to become the above-mentioned posture estimation noise. Inter-part minimum weight distance will be discussed in detail hereinafter.

Based on the part count, maximum-minimum weight computation section 152 computes and holds a maximum value and minimum value of weights as a weight range. Specifically, based on the number of parts (part count) that are subject to comparison by posture estimation section 160 (hereinafter discussed), maximum-minimum weight computation section 152 determines a weight range in such a manner that it becomes wider as the part count increases.

For each posture, per-posture weight processing section 153 determines a small weight or a large weight for each part of a reference model and within the above-mentioned weight range, and thus determines a weight for each part of the reference model. More specifically, of the parts of the reference model, per-posture weight processing section 153 determines small weights for parts for which other parts corresponding to their inter-part minimum weight distances are located within the ranges indicated by those inter-part minimum weight distances. On the other hand, per-posture weight processing section 153 determines large weights for parts for which other parts corresponding to their inter-part minimum weight distances are not located within the ranges indicated by those inter-part minimum weight distances. Weighting may be performed in any of the following units: parts; pixels; ranges including a plurality of pixels. Weighting in units of parts makes for a particularly fast weighting process. Weighting in units of pixels makes for particularly accurate posture estimation. Per-posture weight processing section 153 outputs to posture estimation section 160 weight information indicating the thus determined weights for the parts of the reference model in each posture.

The inter-part minimum weight distance of each part computed by inter-part minimum weight distance computation section 151, and the weight range computed by maximum-minimum weight computation section 152 are values that are common to all postures. Accordingly, inter-part minimum weight distance computation section 151 and maximum-minimum weight computation section 152 need not re-compute these values for each posture, and need instead only retain the computed results.

Based on the body candidate information received from body candidate estimation section 130, posture estimation section 160 shown in FIG. 3 estimates the posture of a person (hereinafter referred to as the "subject") in the image data. For the present embodiment, it is assumed that posture estimation section 160 performs posture estimation based on an estimated likelihood map.

Specifically, for each posture and each part, posture estimation section 160 counts the number of pixels where the position (region) of each part of the reference model indicated by a two-dimensional reference model map overlaps with the position (region) of the corresponding part indicated by an estimated likelihood map. By way of example, let it be assumed that the two-dimensional reference model map holds the value 1 for pixels where a given part is located, and the value 0 for pixels where none are located. Let it further be assumed that the estimated likelihood map holds the value 1 for pixels where a given part is located, and the value 0 for pixels where none are located. In this case, for each part, posture estimation section 160 multiplies the value in the two-dimensional reference model map by the value in the estimated likelihood map on a per pixel basis, and counts the number of pixels whose product is 1.

The two-dimensional reference model map above is information indicating the relative positional relationships among parts when the reference model represented by reference model two-dimensional information is projected onto a predetermined two-dimensional plane. This predetermined two-dimensional plane corresponds to the imaging plane of the camera that captured the image data (in this case, monocular camera 200). The two-dimensional reference model map will be described in detail hereinafter.

For each posture, posture estimation section 160 further multiplies the count value of each part by the weight determined for that part, and sums up the values thus obtained across the entire screen. Based on the sum thus obtained, posture estimation section 160 determines the level of match between the person represented by the estimated likelihood map and the reference model in each posture. Posture estimation section 160 sends, by wire or wirelessly, information to information output apparatus 300 (e.g., a display apparatus), thus notifying the user of the estimation result.

Posture estimation apparatus 100 includes, for example: a CPU; a storage medium (e.g., ROM) storing a control program; and working memory (e.g., RAM). In this case, the functions of the various parts mentioned above are realized by having a control program executed by the CPU.

This posture estimation apparatus 100 is able to, for each part of a reference model, assign a relatively lesser weight to a range (image region) where, when some other part is located thereat, the presence of this other part is likely to become noise with respect to posture estimation.

For a part that overlaps with another part, or that is close in distance to another part (i.e., a crowded area), the probability that it will be estimated accurately by body candidate estimation section 130 becomes low. In particular, for cases where part candidate estimation is carried out by extracting parallel lines, the probability that a crowded area will be estimated accurately becomes low.

As such, posture estimation apparatus 100 performs posture estimation with the significance of crowded areas reduced, and the significance of dispersed areas enhanced. Since posture estimation apparatus 100 thus performs posture estimation with the significance of crowded areas, which might contain a lot of noise, reduced, and the significance of dispersed areas, which characterize a posture, enhanced, it is thus made possible to improve the accuracy of posture estimation.

Whereas human posture involves a high degree of freedom, only limited and representative postures can be prepared as reference models in reality. Accordingly, as the part count increases, miniscule structural differences of postures, which are to be returned as estimation results, tend to accumulate with respect to posture reference models that are to serve as estimation results.

As such, as the part count increases, posture estimation apparatus 100 increases the difference between the weight for a crowded area and the weight for a dispersed area. Posture estimation apparatus 100 is thus able to ensure that a significant difference in a given part is not overlooked, while performing posture estimation in which the influences of miniscule differences are suppressed. In other words, posture estimation apparatus 100 is capable of further improving posture estimation accuracy.

Before describing an operation of posture estimation apparatus 100, body constraint information and reference model examples will now be described.

An example of the body constraint information stored in body constraint information storage section 110 will first be described.

By way of example, with at least one of the length of a predetermined part and the angle of a joint as a reference, body constraint information limits the region in which a part that articulates with the predetermined part may lie (i.e., the part region). In this case, the body constraint information includes at least one of a ratio of a given part's length to another part's length and the angle range of motion of a joint, for example. The body constraint information may specify that, where the shoulder width is defined as being 1, the length of the upper arm is 0.6, for example.

By way of example, the body constraint information includes information that describes, for each part, a part length ratio and freedom of movement in three directions (X-axis direction, Y-axis direction, and Z-axis direction) where the joint closer to the torso is taken to be the pivot point.

For the body constraint information, assuming, for example, that the part ID) for the right upper arm is "3" and that the ratio of the part length of the right upper arm to the part length of the shoulders is "0.8," the part length of the right upper arm may be specified by a file or program source written as follows.

```
Begin
    Part ID: 3
    Length ratio: 0.8
End
```

For the body constraint information, assuming, for example, that the part ID for the right upper arm is "3" and that the ratio of the thickness of the right upper arm to the part length of the shoulders is "0.2," the part thickness of the right upper arm may be specified by a file or program source written as follows.

```
Begin
    Part ID: 3
    Thickness ratio: 0.2
End
```

Furthermore, it is assumed, for example, that the joint U) for the right shoulder is "100," that the part ID for the shoulders is "1," and that the part ID for the right upper arm is "3." It is also assumed that the movable directions of the right upper arm are (−60.0, 90.0) with respect to the X-axis, (−90.0, 90.0) with respect to the Y-axis, and (−90.0, 90.0) with respect to the Z-axis. In this case, the body constraint information may specify the freedom of the right upper arm with respect to the right shoulder joint by a file or program source written as follows, for example.

```
Begin
    Joint ID: 100
    Part ID: 1
    Part ID: 3
    Movable directions: rx, ry, rz
    Angles: (−60.0, 90.0), (−90.0, 90.0), (−90.0, 90.0)
End
```

For the cases above, the information indicating the articular relationship between joints and parts represented by joint IDs and part IDs, and the information indicating the movable directions and angles of each joint may be written in separate files.

The body constraint information may also be written in terms of information obtained by projecting each position onto a two-dimensional coordinate system. In this case, even if the positional information is unique three-dimensionally, its value may vary depending on the projection angle. Furthermore, movable directions and angles would be two-dimensional values. Accordingly, if body constraint information storage section 110 is to hold such values as body constraint information, then it must also hold information regarding projection angle.

This concludes this description of body constraint information examples.

Reference model examples will now be described.

A reference model includes, for example, reference model three-dimensional information and reference model two-dimensional information regarding that reference model three-dimensional information.

The reference model three-dimensional information includes first-stage information that represents a reference model for each posture state through part positions, joint positions, and/or the like with respect to a three-dimensional coordinate system. The reference model two-dimensional information includes second-stage information that represents a reference model in the posture state indicated by the reference model three-dimensional information through part positions, joint positions, and/or the like with respect to a two-dimensional coordinate system. In other words, the reference model two-dimensional information includes information that indicates relative positional relationships of the joints and/or the like as viewed from a given perspective (i.e., as projected onto a given two-dimensional plane).

In the case above, the reference model two-dimensional information is obtained by projecting the reference model three-dimensional information onto a two-dimensional coordinate system. Furthermore, if a plurality of perspectives are defined for a reference model in a single posture state, a plurality of sets of reference model two-dimensional information may be generated for one set of reference model three-dimensional information. The existence of a plurality of perspectives signifies the existence of a plurality of position and orientation combinations for the reference model with respect to camera perspective.

The reference model three-dimensional information will first be described.

The reference model three-dimensional information is expressed using a predetermined three-dimensional coordinate system which takes the joint position of the right shoulder joint to be its origin, and which defines the distance between the right shoulder position and the left shoulder position as being 1. The reference model three-dimensional information may also be expressed using a coordinate system that takes some other position to be its origin, or a coordinate system that defines some other length (e.g., a part length of the arms, the person's height, and/or the like) as being 1.

Let it be assumed, for example, that the posture ID for the posture state is "200," that the joint ID for the right shoulder is "100," that the part ID for the shoulders is "1," and that the part ID for the right upper arm is "3." Let it further be assumed that the movable directions of the right upper arm are (20.0) with respect to the X-axis, (90.0) with respect to the Y-axis, and (0.0) with respect to the Z-axis. In this case, the reference model three-dimensional information may specify the freedom of the right upper arm of the reference model with respect to the right shoulder joint by a file or program source written as follows, for example. The reason the movable directions of the reference model three-dimensional information are, unlike those of the body constraint information, unidirectional instead of being ranges is because the reference model three-dimensional information is information specific to each posture state. However, the movable directions of the reference model three-dimensional information may also be defined with a range, taking joint angle errors and individual differences into consideration.

```
Begin three-dimensional posture
    Posture ID: 200
    Begin joint
        Joint ID: 100
        Part ID: 1
        Part ID: 3
        Movable directions: rx, ry, rz
        Angles: 20.0, 90.0, 0.0
        Position: (0, 0, 0)
    End joint
End three-dimensional posture
```

For the reference model three-dimensional information, information regarding joints and information regarding parts may be written in separate files. This allows files to be shared among a plurality of posture states, thus reducing the size of reference model storage section 140.

For the reference model three-dimensional information, the correspondence relationship between joint positions and posture states and the correspondence relationship between joint angles and posture states may be written in separate files. Thus, in preparing the reference model three-dimensional information for a plurality of reference models of varying body types, a file describing the correspondence relationship between joint angles and posture states may be used as a common/shared file. Accordingly, the size of reference model storage section 140 may be reduced.

The reference model three-dimensional information may include joint angles, part lengths, part thicknesses, and/or the like, while omitting joint positions. In this case, joint positions may be computed based on joint angles and body constraints. Thus, the size of reference model storage section 140 may be reduced.

By way of example, the reference model three-dimensional information regarding the right upper arm mentioned above may be separated and written as follows.

```
Begin three-dimensional posture definition
    Posture ID: 200
    Begin joint
        Joint ID: 100
        Part ID: 1
        Part ID: 3
        Movable directions: rx, ry, rz
    End joint
End three-dimensional posture definition
Begin three-dimensional posture angle
    Posture ID: 200
    Begin joint
        Joint ID: 100
        Angles: 20.0, 90.0, 0.0
    End joint
End three-dimensional posture angle
Begin three-dimensional posture position
    Posture ID: 200
    Begin joint
        Joint ID: 100
        Position: (0, 0, 0)
    End joint
End three-dimensional posture position
```

For the reference model three-dimensional information, information regarding a plurality of joints may be included in a single file as follows. In this case, angles and positions may be expressed by means of a predetermined three-dimensional coordinate system which takes a given reference point (e.g., the right shoulder joint position, and/or the like) to be its origin. Alternatively, angles and positions may be expressed by means of a relative three-dimensional coordinate system that references the joint position that is closer to the torso and the axial direction of another part that is closer to the torso.

```
Begin three-dimensional posture
    Posture ID: 200
    Begin joint
        Joint ID: 100
        Part ID: 1
        Part ID: 3
        Movable directions: rx, ry, rz
        Angles: 20.0, 90.0, 0.0
        Position: (0, 0, 0)
    End joint
    Begin joint
    ...
    End joint
End three-dimensional posture
...
Begin three-dimensional posture
    Posture ID: 300
    Begin joint
    ...
    End joint
    Begin joint
    ...
    End joint
End three-dimensional posture
```

The reference model three-dimensional information may be written in separate files for each information type as provided above even when information regarding a plurality of joints is thus included in a single file.

Similarly, for the reference model three-dimensional information, information regarding a plurality of posture states may be included in a single file.

The reference model two-dimensional information will now be described.

The reference model two-dimensional information is generated based on the reference model three-dimensional information. The reference model two-dimensional information may be pre-generated and stored in reference model storage section 140, and/or it may be generated, as needed, by reference model storage section 140, weight computation section 150, posture estimation section 160, and/or the like based on the reference model three-dimensional information. If a plurality of perspectives are defined, the size of reference model storage section 140 may be reduced by arranging for the reference model two-dimensional information to be generated as needed. The reference model two-dimensional information may be generated by reference model storage section 140, for example. It is assumed that information indicating how many pixels in the image the reference part length amounts to is added to the reference model two-dimensional information.

By way of example, let it be assumed that, as projected onto two-dimensional coordinates, the angle of the horizontal direction is "90 degrees," the angle of the perpendicular direction is "45 degrees," the reference part is the shoulders, and the length of the shoulders (the distance from the right shoulder joint position to the left shoulder joint position) is "20 pixels." In this case, the reference model two-dimensional information regarding the right upper arm mentioned above may be written as follows, where it is assumed that the two-dimensional coordinate system takes the horizontal direction in the image to be the x-axis, the perpendicular direction to be the y-axis, and the right shoulder joint position to be the origin, and that the angle is relative to the x-axis. The projection angle is used to narrow down the reference model two-dimensional information based on the installation angle of monocular camera 200, for example.

```
Begin two-dimensional posture
    Posture ID: 200
    Length conversion for reference part: 20
    Begin projection
        Projection angle: (90, 45)
        Begin joint
            Joint ID: 100
            Part ID: 1
            Part ID: 3
            Angle: 10.0
            Position: (0, 0)
        End joint
    End projection
End two-dimensional posture
```

As in the case of the reference model three-dimensional information mentioned above, the reference model two-dimensional information may be written in separate files for each image posture state or each information type.

Furthermore, as provided below, the reference model two-dimensional information may include information regarding a plurality of joints with respect to a single projection angle, and/or information regarding a plurality of projection angles with respect to a single posture.

```
Begin two-dimensional posture
    Posture ID: 200
    Length conversion for reference part: 20
    Begin projection
        Projection angle: (90, 45)
        Begin joint
            Joint ID: 100
            Part ID: 1
            Part ID: 3
            Angle: 10.0
            Position: (0, 0)
        End joint
        ...
        Begin joint
        ...
        End joint
    End projection
    Begin projection
        Projection angle: (70, 45)
        Begin joint
        ...
        End joint
    End projection
    ...
End two-dimensional posture
```

The reference model two-dimensional information may be written in separate files for each image posture state or each information type as in the case of the reference model three-dimensional information provided above even when information regarding a plurality of projection angles is included with respect to a single posture. Thus, the size of reference model storage section 140 may be reduced.

The projection angle onto a two-dimensional coordinate system for converting the reference model three-dimensional information into the reference model two-dimensional information may be a fixed value, and it may also be a value that varies in accordance with a computed gradient.

The reference model two-dimensional information may also include a two-dimensional reference model map. This two-dimensional reference model map includes a map that represents, in an image of a predetermined size, a posture described by two-dimensional information, and that identifies pixels of each reference model that are to be weighted.

The two-dimensional reference model map may be computed by, for example, projecting, based on the reference model three-dimensional information, a three-dimensional object, which is obtained by giving some thickness to each part, onto a plane from the projection direction included in the reference model two-dimensional information. Furthermore, the two-dimensional reference model map may be computed by, based on the reference model two-dimensional information, taking the interior of a rectangular region having the thickness and length of each part to be the pixels for that part. Furthermore, the two-dimensional reference model map may be computed by, based on the reference model two-dimensional information, taking the pixels of an axis connecting the joints of each part, or a single point at the center of each part, or a region including that single point, to be the pixels of that part.

The two-dimensional reference model map includes, for each pixel, information as to which part the pixel is included in. Specifically, the two-dimensional reference model map includes map information including, for each pixel and each part, a flag that assumes a value of 1 if it is included in that part, or a value of 0 if not.

If only a two-dimensional posture is to be derived as an estimation result, posture estimation apparatus 100 does not necessarily have to hold reference model three-dimensional information. Furthermore, the two-dimensional reference model map may be pre-generated and stored in reference model storage section 140. Furthermore, the two-dimensional reference model map may be generated, as needed, by reference model storage section 140, weight computation section 150, posture estimation section 160, and/or the like based on the reference model two-dimensional information.

This concludes this description of reference model examples.

Operations of posture estimation apparatus 100 will now be described.

Figure 7:
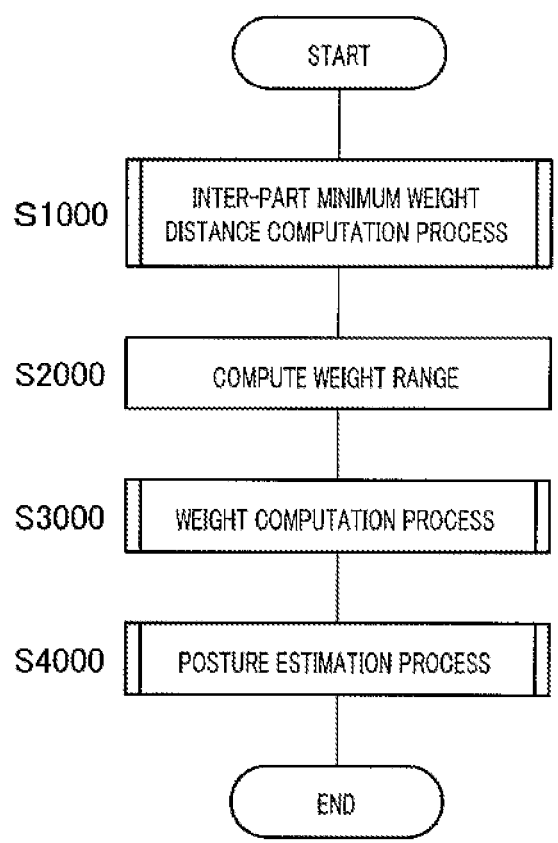
FIG. 7 is a flowchart showing an operation example of a posture estimation apparatus according to Embodiment 3.

FIG. 7 is a flowchart showing an operation example of posture estimation apparatus 100.

First, in step S1000, posture estimation apparatus 100 executes an inter-part minimum weight distance computation process. The inter-part minimum weight distance computation process is a process that computes and determines, based on body constraint information, an inter-part minimum weight distance for each part.

Figure 8:
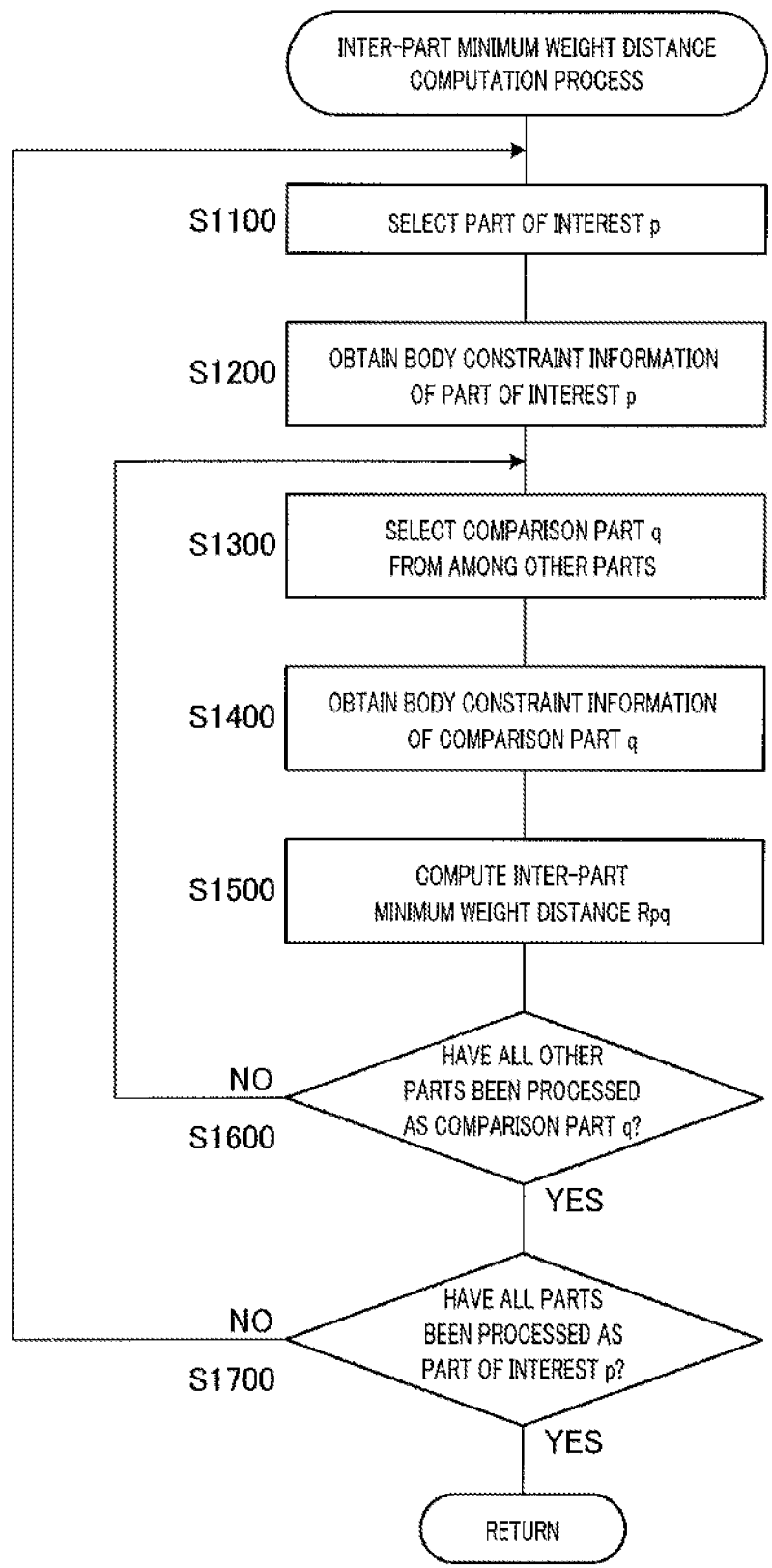
FIG. 8 is a flowchart showing an example of an inter-part minimum weight distance computation process with respect to Embodiment 3.

FIG. 8 is a flowchart showing an example of an inter-part minimum weight distance computation process.

First, in step S1100, inter-part minimum weight distance computation section 151 selects one part of interest p from among parts that are subject to evaluation.

In step S1200, inter-pert minimum weight distance computation section 151 then obtains information that is necessary for inter-part minimum weight distance computation from the body constraint information of part of interest p that is currently selected.

In step S1300, inter-part minimum weight distance computation section 151 then selects, of the parts that are subject to evaluation, comparison part q from among parts other than part of interest p that is currently selected (hereinafter referred to as "the other parts").

In step S1400, inter-part minimum weight distance computation section 151 then obtains information that is necessary for inter-part minimum weight distance computation from the body constraint information of comparison part q that is currently selected.

In step S1500, inter-part minimum weight distance computation section 151 then computes inter-part minimum weight distance Rpq based on the body constraint information of part of interest p that is currently selected and on the body constraint information of comparison part q that is currently selected. Inter-part minimum weight distance computation section 151 stores thus-computed inter-part minimum weight distance Rpq in such a manner as to be mapped to the combination of part of interest p that is currently selected and comparison part q that is currently selected.

An example of an inter-part minimum weight distance computation method will now be described.

FIGS. 9A through 9E show schematic diagrams of reference model examples and examples of a person represented by estimated likelihood maps.

Human posture involves a significant degree of freedom with variability in the position of each part, and it is difficult to prepare reference models that encompass all possible variations in the position of each part. For purposes of convenience, for the case at hand, it is assumed that only reference model 413-1 of a first posture shown in FIG. 9A, and reference model 413-2 of a second posture shown in FIG. 9B exist. It is further assumed that an estimated likelihood map for person 414 shown in FIG. 9C is obtained.

Figure 9E:
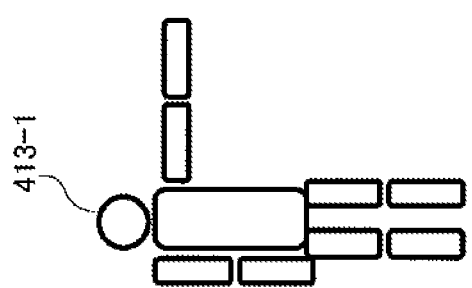
FIGS. 9A through 9E show schematic diagrams of reference model examples and examples of an object represented by an estimated likelihood map with respect to Embodiment 3.
Figure 9D:
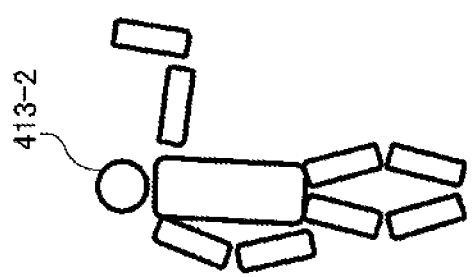
Figure 9C:
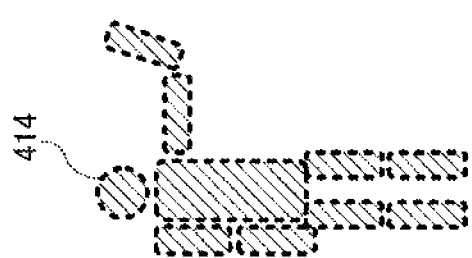
Figure 9B:
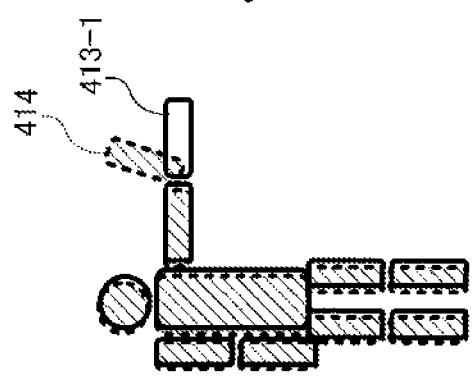
Figure 9A:
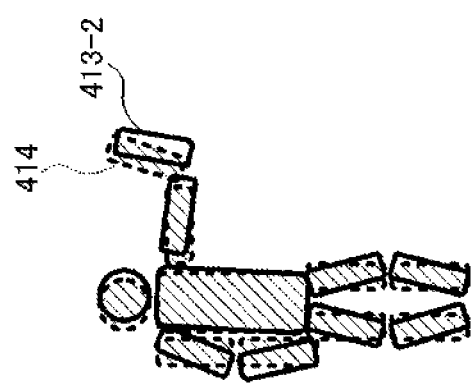

It is assumed that, apart from the forearm that is bent upward, the degree of match is high with respect to reference model 413-1 of the first posture as shown in FIG. 9D, and that the degree of match is low with respect to reference model 413-2 of the second posture as shown in FIG. 9E.

In the present embodiment, posture estimation section 160 performs posture estimation based on the number of matching pixels counted on a per part basis as mentioned above. Accordingly, in the case of FIG. 9E, if each part is treated equally, errors will accumulate when a comparison is made with respect to reference model 413-2 of the second posture. Consequently, as a whole, the degree of match with respect to reference model 413-2 of the second posture could turn out to be lower than the degree of match with respect to reference model 413-1 of the first posture.

However, what characterizes the posture of person 414 is mainly the forearm that is bent upward. Accordingly, reference model 413-2 of the second posture with the forearm similarly bent upward is the estimation result that should be obtained.

As such, posture estimation apparatus 100 according to the present embodiment sets a greater weight for dispersed areas than it does for crowded areas as mentioned above. Thus, in the example in FIG. 9, the focus is placed on the degree of match with regard to the forearm bent upward, and reference model 413-2 of the second posture is consequently obtained as an estimation result. In other words, posture estimation accuracy improves.

A crowded area includes a part of a reference model that is close in distance to another part. On the other hand, a dispersed area includes a part of a reference model that is far apart in distance from another part. Accordingly, through a method such as that below, for example, inter-part minimum weight distance computation section 151 computes an inter-part minimum weight distance as a reference for differentiating between crowded areas and dispersed areas.

Figure 10:
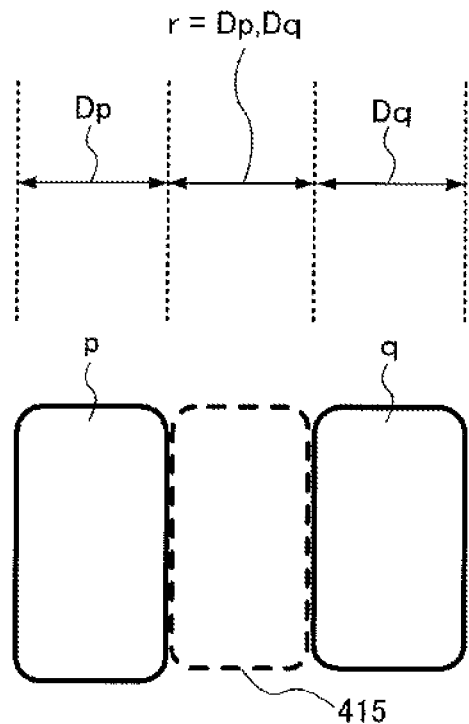
FIG. 10 is a first diagram illustrating a first example of an inter-part minimum weight distance computation method with respect to Embodiment 3.
Figure 11:
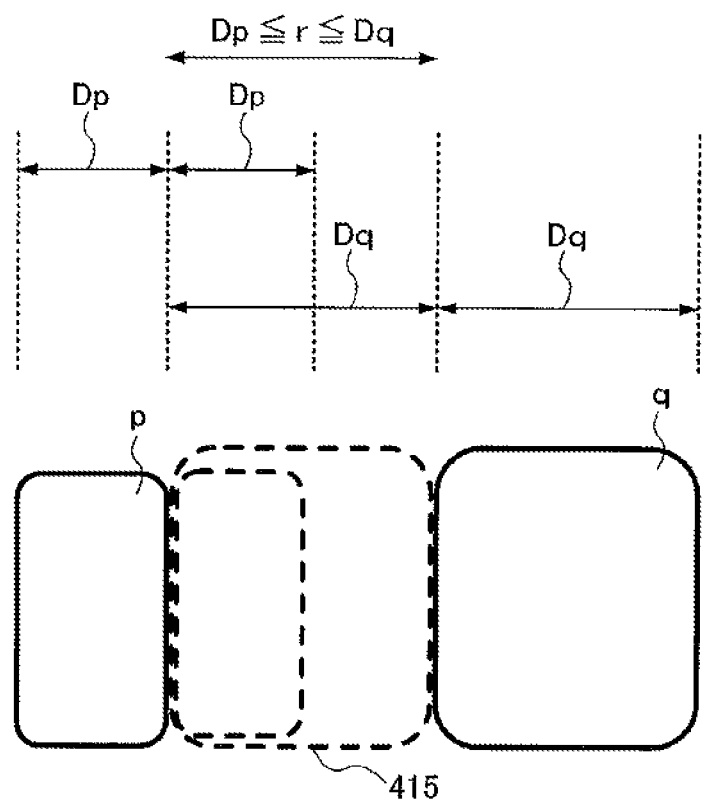
FIG. 11 is a second diagram illustrating a second example of an inter-part minimum weight distance computation method with respect to Embodiment 3.

FIG. 10 and FIG. 11 are diagrams illustrating examples of an inter-part minimum weight distance computation method.

As shown in FIG. 10 and FIG. 11, it is assumed that part of interest p of part thickness Dp, and comparison part q of part thickness Dq exist in a reference model. FIG. 10 shows a case where part thickness Dp and part thickness Dq are identical, whereas FIG. 11 shows a case where they are not. Part thicknesses Dp and Dq are included in the body constraint information stored in body constraint information storage section 110, for example.

Depending on the posture, distance r between part of interest p and comparison part q may sometimes become close to at least one of part thickness Dp and part thickness Dq. If such is the case, for part candidate extraction that is based on the detection of a pair of two parallel lines in particular, a pair including the inner edge of part of interest p and the inner edge of comparison part q becomes a pair of parallel lines that satisfies the condition of part thickness Dp, Dq. Accordingly, space 415 between the inner edge of part of interest p and the inner edge of comparison part q could potentially be erroneously estimated as a part region of part of interest p or comparison part q.

Conversely, if distance r is sufficiently greater than both part thicknesses Dp and Dq, it is unlikely that space 415 would be erroneously estimated as a part region of part of interest p or comparison part q.

As such, with respect to each part of the reference model, inter-part minimum weight distance computation section 151 computes the inter-part minimum weight distance based on the respective part thicknesses and the distance with regard to when the part is combined with another part. Specifically, inter-part minimum weight distance computation section 151 computes inter-part minimum weight distance Rpq between part of interest p of part thickness Dp and comparison part q of part thickness Dq using Equation (1) below, for example.

$$Rpq = a \times Dp + b \times Dq \quad \text{(Equation 1)}$$

Parameters a and b above are constants that may be defined arbitrarily in accordance with the accuracy demanded for posture estimation or with the environmental conditions under which posture estimation apparatus 100 is employed. By way of example, if Dp≤Dq, then a=0 and b=1. For example, parameters a and b should be set higher for an environment where heavily clothed people or people of varying body types might become subjects as compared to an environment where only lightly clothed people with similar body types become subjects. Thus, robustness of posture estimation may be improved.

However, human posture involves a significant degree of freedom with variability in the angle of each part, and it is difficult to prepare reference models that encompass all possible variations in the angle of each part. Accordingly, posture estimation apparatus 100 ignores a certain range of angle errors, and estimates the closest posture. It is preferable that inter-part minimum weight distance computation section 151 compute inter-part minimum weight distance Rpq taking such angle errors into consideration.

Figure 12:
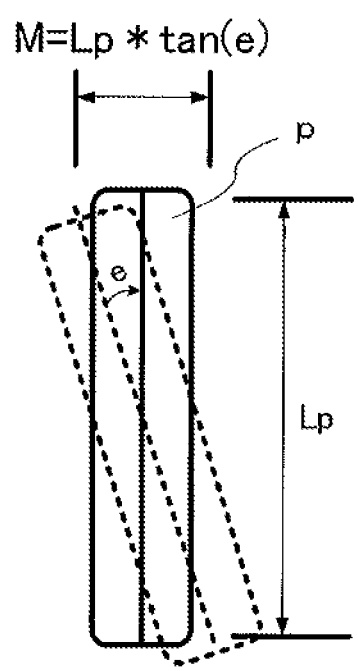
FIG. 12 is a diagram illustrating a third example of an inter-part minimum weight distance computation method with respect to Embodiment 3.

FIG. 12 is a diagram illustrating an example of an inter-part minimum weight distance computation method that takes angle errors into consideration.

As shown in FIG. 12, with respect to part of interest p, assuming its part length is Lp, and that the maximum value of angle error (angle error to be ignored) is e, part position offset M is, at most, Lp×tan(e). Similarly, although not shown in the drawing, with respect to comparison part q, assuming its part length is Lq, its position might possibly be off by Lq×tan(e).

Accordingly, inter-part minimum weight distance computation section 151 computes inter-part minimum weight distance Rpq between part of interest p of part thickness Dp and comparison part q of part thickness Dq using Equation (2) below, for example. Part thicknesses Dp and Dq, part length Lq, and maximum value e of angle error may be included in the body constraint information stored by body constraint information storage section 110, for example.

$$Rpq = a \times Dp + b \times Dq + c \times Lp \times \tan(e) + d \times Lq \times \tan(e) \quad \text{(Equation 2)}$$

Parameters a through d above are constants that may be defined arbitrarily in accordance with the accuracy demanded for posture estimation or with the environmental conditions under which posture estimation apparatus 100 is employed.

In other words, when Equation (2) is used, inter-part minimum weight distance computation section 151 is able to compute the inter-part minimum weight distance based on the part thicknesses and lengths of the respective parts, and the angle error to be ignored between the parts.

Through a method such as that above, inter-part minimum weight distance computation section 151 is able to compute an inter-part minimum weight distance as a value that accurately indicates a range where, when some other part is located thereat, the presence of this other part is likely to become noise with respect to posture estimation.

This concludes this description of an example of an inter-part minimum weight distance computation method.

In step S1600 in FIG. 8, inter-part minimum weight distance computation section 151 determines whether or not all of the other parts have been processed as comparison part q. If any of the other parts have not yet been processed as comparison part q (S1600: NO), inter-part minimum weight distance computation section 151 returns to step S1300, selects the next part among the other parts and repeats the process. On the other hand, if all of the other parts have been processed as comparison part q (S1600: YES), inter-part minimum weight distance computation section 151 proceeds to step S1700.

In step S1700, inter-part minimum weight distance computation section 151 determines whether or not all parts subject to evaluation have been processed as part of interest p. If there are any parts that have not yet been processed as part of interest p (S1700: NO), inter-part minimum weight distance computation section 151 returns to step S1100, selects the next part and repeats the process. On the other hand, if all parts have been processed as part of interest p (S1700: YES), inter-part minimum weight distance computation section 151 returns to the process in FIG. 7.

In step S2000 in FIG. 7, posture estimation apparatus 100 computes a weight range at maximum-minimum weight computation section 152.

An example of a weight range computation method will now be described.

As the part count increases, the degree of freedom of human posture increases, and the cumulative error in the positions of the parts within a range that may be considered to be the same posture increases. As such, maximum-minimum weight computation section 152 computes minimum weight Wmin and maximum weight Wmax that satisfy Equation (3) below, for example, and takes the range from minimum weight Wmin to maximum weight Wmax to be the weight range.

$$e' \times (n-1) \times W\min < c \times W\max \quad \text{(Equation 3)}$$

n in the equation above denotes the part count, u the target resolution (frequency), and e' the positional error range (frequency of matching pixels). Part count n is the total number of parts subject to evaluation as mentioned above, and may be 10, for example. Target resolution u and parameter c are constants that may be defined arbitrarily in accordance with the accuracy demanded for posture estimation or with the environmental conditions under which posture estimation apparatus 100 is employed. Error range e' may be included in the body constraint information stored by the body constraint information storage section 110, for example.

Through a method such as that above, maximum-minimum weight computation section 152 is able to determine a weight range in such a manner that it becomes wider as the part count increases. In other words, with respect to a posture that results in errors that fall within a given error range except for some of the parts, maximum-minimum weight computation section 152 is able to assign weights in such a manner as not to cancel out the target resolution for the rest of the parts. Specifically, maximum-minimum weight computation section 152 may determine maximum weight Wmax with minimum weight Wmin fixed at 1, or it may determine minimum weight Wmin with maximum weight Wmax fixed at 1. Maximum-minimum weight computation section 152 may also determine the values of minimum weight Wmin and maximum weight Wmax in such a manner that their sum would be 1.

This concludes this description of an example of a weight range computation method.

In step S3000, posture estimation apparatus 100 executes a weight computation process. The weight computation process is a process that computes and determines, based on the inter-part minimum weight distance of each part, a weight for each part of each reference model.

Figure 13:
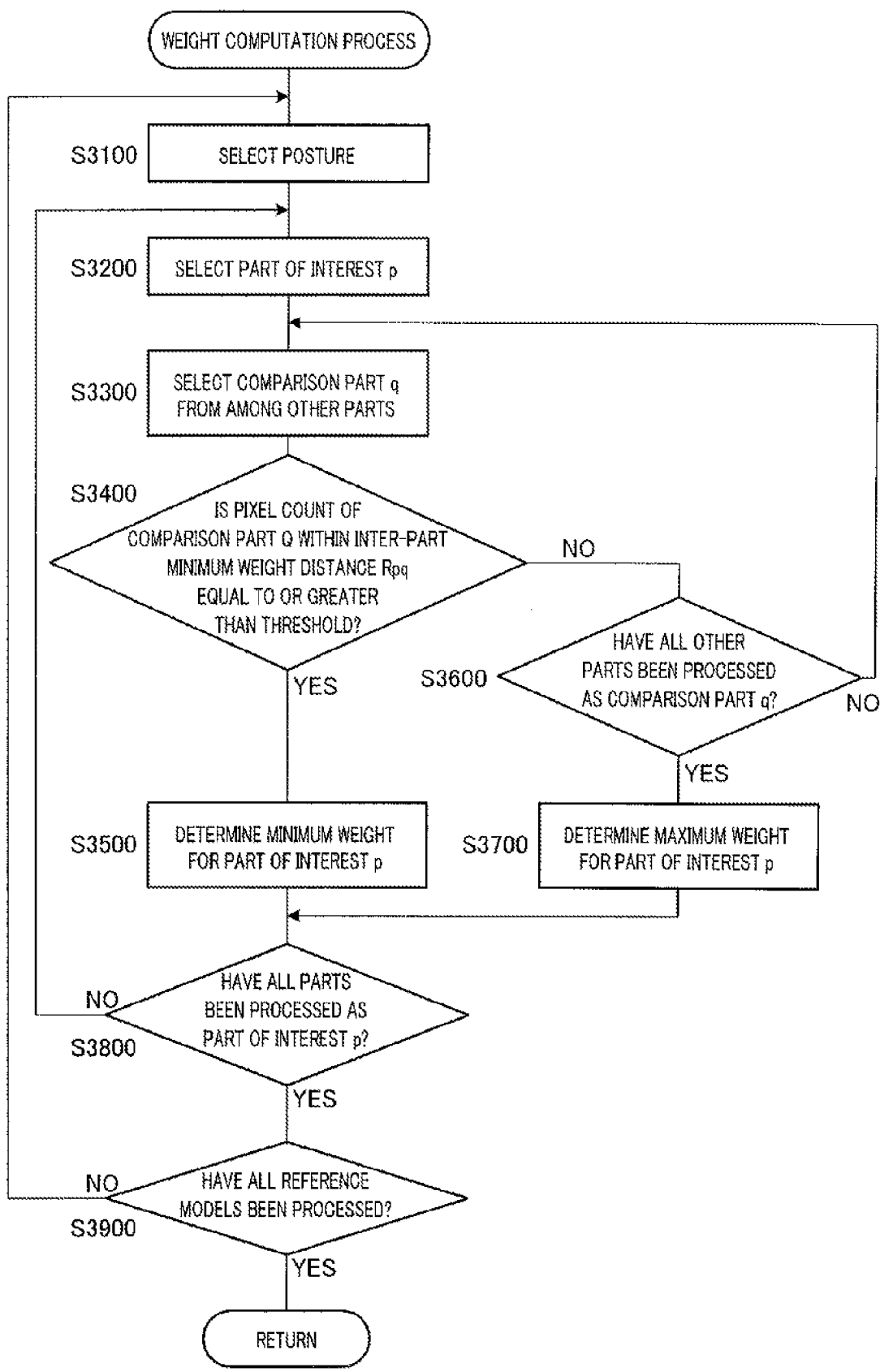
FIG. 13 is a flowchart showing an example of a weight computation process with respect to Embodiment 3.

FIG. 13 is a flowchart showing an example of the weight computation process.

First, in step S3100, per-posture weight processing section 153 selects one posture from among postures that are subject to evaluation.

In step S3200, per-posture weight processing section 153 selects one part of interest p from among parts that are subject to evaluation.

In step S3300, per-posture weight processing section 153 selects comparison part q from among the other parts.

In step S3400, per-posture weight processing section 153 counts the number of pixels of comparison part q within the range indicated by inter-part minimum weight distance Rpq corresponding to the combination of part of interest p that is currently selected and comparison part q that is currently selected. It is then determined whether or not the thus counted number of pixels is equal to or greater than a predetermined threshold. This predetermined threshold is a value corresponding to determination criteria for the degree of match of parts at posture estimation section 160. In other words, based on whether or not the pixel count is equal to or greater than the predetermined threshold, per-posture weight processing section 153 determines whether or not comparison part q that is currently selected is located within the range indicated by inter-part minimum weight distance Rpq.

The predetermined threshold mentioned above may be defined as a proportion relative to the number of pixels included in each part of a two-dimensional reference model map, for example. If the threshold is defined as being 50%, and the number of pixels included in a given part of a two-dimensional reference model map is 100, per-posture weight processing section 153 would determine whether the number of pixels counted is equal to or greater than 50. When the threshold is raised, the probability that a part is included within inter-part minimum weight distance Rpq increases accordingly. When the threshold is lowered, the proportion of parts included within inter-part minimum weight distance Rpq decreases accordingly.

If the above-mentioned pixel count is equal to or greater than the predetermined threshold (S3400: YES), per-posture weight processing section 153 proceeds to step S3500. This, in other words, signifies that, with respect to the currently selected posture, comparison part q that is currently selected is located within the range indicated by inter-part minimum weight distance Rpq for part of interest p that is currently selected.

On the other hand, if the above-mentioned pixel count is less than the predetermined threshold (S3400: NO), per-posture weight processing section 153 proceeds to step S3600. This, in other words, signifies that, with respect to the currently selected posture, comparison part q that is currently selected is not located within the range indicated by inter-part minimum weight distance Rpq for part of interest p that is currently selected.

In step S3500, per-posture weight processing section 153 determines, from the weight range, minimum weight Wmin to be the weight for part of interest p that is currently selected. In other words, per-posture weight processing section 153 assigns minimum weight Wmin to any part for which even one other part is located within the range indicated by its inter-part minimum weight distance.

On the other hand, in step S3600, per-posture weight processing section 153 determines whether or not all of the other parts have been processed as comparison part q. If any of the other parts have not yet been processed as comparison part q (S3600: NO), per-posture weight processing section 153 returns to step S3300, selects the next part among the other parts and repeats the process. On the other hand, if all of the other parts have been processed as comparison part q (S3600: YES), per-posture weight processing section 153 proceeds to step S3700.

In step 3700, per-posture weight processing section 153 determines, from the weight range, maximum weight Wmax to be the weight for part of interest p that is currently selected. In other words, per-posture weight processing section 153 assigns maximum weight Wmax to any part for which no other part is located within the range indicated by its inter-part minimum weight distance.

In step S3800, per-posture weight processing section 153 determines whether or not all parts subject to evaluation have been processed as part of interest p. If there are any parts that have not yet been processed as part of interest p (S3800: NO), per-posture weight processing section 153 returns to step S3200, selects the next part and repeats the process. On the other hand, if all parts have been processed as part of interest p (S3800: YES), per-posture weight processing section 153 proceeds to step S3900.

In step S3900, per-posture weight processing section 153 determines whether or not all postures subject to evaluation have been processed. If there are any postures subject to evaluation that have not yet been processed (S3900: NO), per-posture weight processing section 153 returns to step S3100, selects the next posture and repeats the process. On the other hand, if all postures subject to evaluation have been processed (S3900: YES), per-posture weight processing section 153 outputs, as weight information, information in which identifiers of parts and the respective weight values assigned to those parts are arranged in a list, and returns to the process in FIG. 7.

In step S4000 in FIG. 7, posture estimation apparatus 100 executes a posture estimation process. The posture estimation process is a process that estimates the posture of a person included in image data by applying weights that have been determined.

Figure 14:
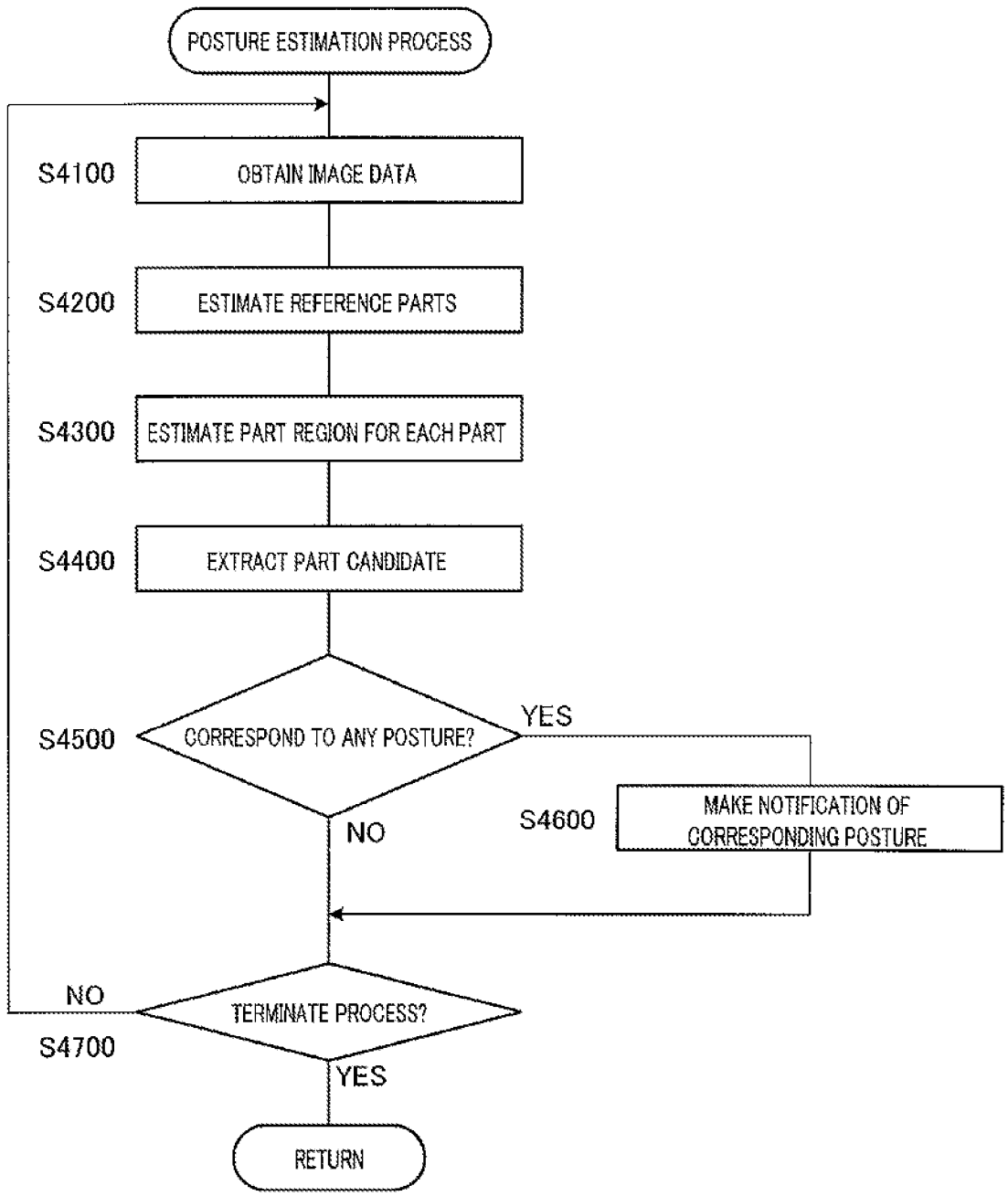
FIG. 14 is a flowchart showing an example of a posture estimation process with respect to Embodiment 3.

FIG. 14 is a flowchart showing an example of a posture estimation process.

First, in step S4100, part region estimation section 131 of body candidate estimation section 130 obtains one still image's worth of image data from monocular camera 200 via image data acquisition section 120.

In step 4200, part region estimation section 131 then performs a process of estimating the positions and orientation of reference parts (hereinafter referred to as "reference part estimation process").

An example of the details of the reference part estimation process will now be described. Broadly speaking, the reference part estimation process includes a first process of estimating the shoulder joint positions of a person, and a second process of estimating the orientation of the torso of a person.

The first process of estimating the shoulder joint positions of a person will be described first.

Part region estimation section 131 detects an omega shape from the image data, and estimates shoulder joint positions based on the omega shape.

Figure 15:
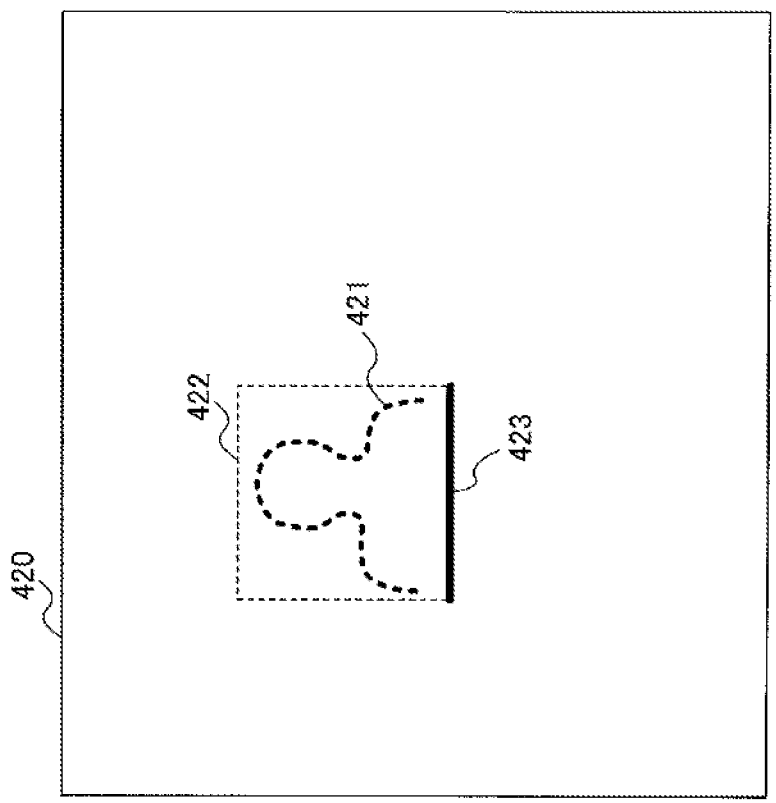
FIG. 15 is diagram illustrating an omega shape with respect to Embodiment 3.

FIG. 15 is a diagram illustrating an omega shape.

An omega ($\Omega$) shape is a characteristic edge shape of a region that encompasses the head and shoulders of a person, and is a shape having a high probability that, with regard to the human body, imaging would be carried out most stably when a surveillance camera or the like is used. Further, the positions of the head and shoulders relative to the torso of a person vary little. Accordingly, part region estimation section 131 first detects an omega shape to detect the positions of the head and shoulders of a person. It then estimates part regions for other parts relative thereto, thus accurately estimating part regions.

An omega shape may be detected using a detector created with Real AdaBoost and/or the like using a sufficient number of sample images, for example. Examples of features used for the detector may include histogram of gradient (HoG) features, Sparse features, Haar features, and/or the like. Besides boosting algorithms, other learning algorithms such as support vector machines (SVMs), neural networks, and/or the like may also be employed.

Part region estimation section 131 first detects omega shape 421 from image 420 of the image data. Of the pixels in omega region 422, the pixels forming omega shape 421 (the pixels at the edge portion) are of a digital signal of "1," while the rest of the pixels are of a digital signal of "0." A relatively small rectangular region encompassing omega shape 421 is determined to be omega region 422. The base of omega region 422 is referred to as reference line 423.

Part region estimation section 131 eliminates noise contained in omega region 422. Specifically, of the pixels in omega region 422, part region estimation section 131 deems any digital signal of "1" that is present within the region enclosed by omega shape 421 to be noise and corrects it to a digital signal of "0." This correction may be done by performing a so-called closing process, for example. A closing process is a process that enlarges or reduces an image region by a predetermined number of pixels or by a predetermined proportion. Through this correction, the accuracy of the distance histogram discussed hereinafter may be improved.

Part region estimation section 131 obtains the perpendicular distance from reference line 423 to omega shape 421 at various positions along reference line 423.

Figure 16:
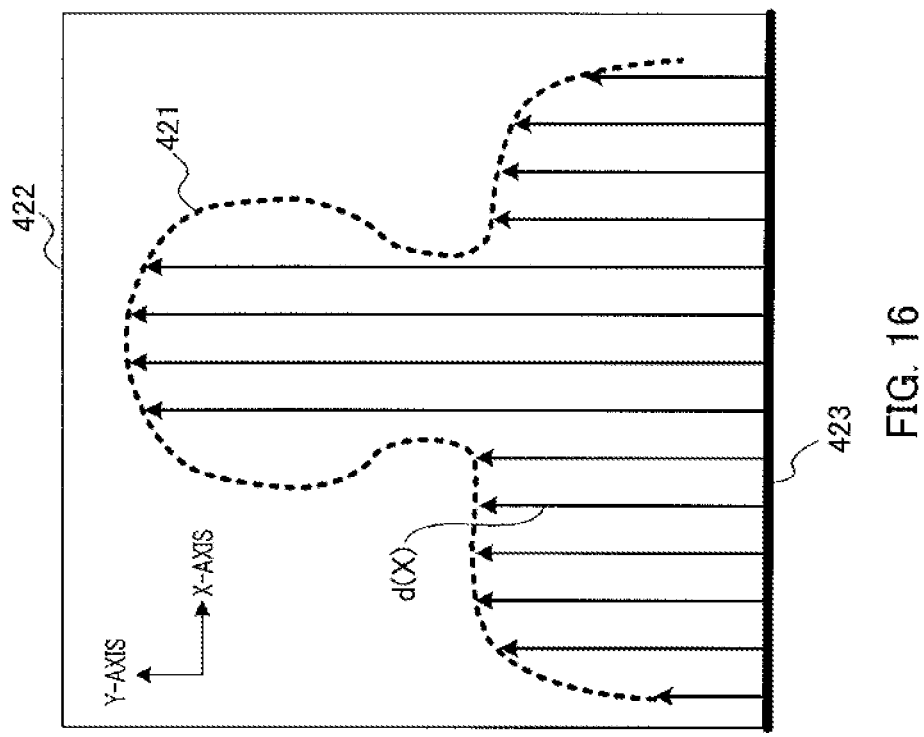
FIG. 16 is a diagram illustrating perpendicular distances from a reference line to an omega shape with respect to Embodiment 3.

FIG. 16 is a diagram illustrating perpendicular distances from reference line 423 to omega shape 421.

As shown in FIG. 16, part region estimation section 131 treats the direction of reference line 423 as the X-axis, and the direction perpendicular to reference line 423 as the Y-axis. Part region estimation section 131 takes the pixel count from the left end of reference line 423 to be the X-coordinate, for example. Part region estimation section 131 acquires, as perpendicular distance d(X), the pixel count in the Y-axis direction from reference line 423 to the pixel forming omega shape 421, that is, the perpendicular distance to omega shape 421. By "the pixel forming omega shape 421," what is meant, for example, is the pixel closest to reference line 423 among pixels with a digital signal of "1."

Part region estimation section 131 generates a distance histogram where n items of perpendicular distance d(X) data are mapped to X-coordinates (where n is a positive integer).

Figure 17:
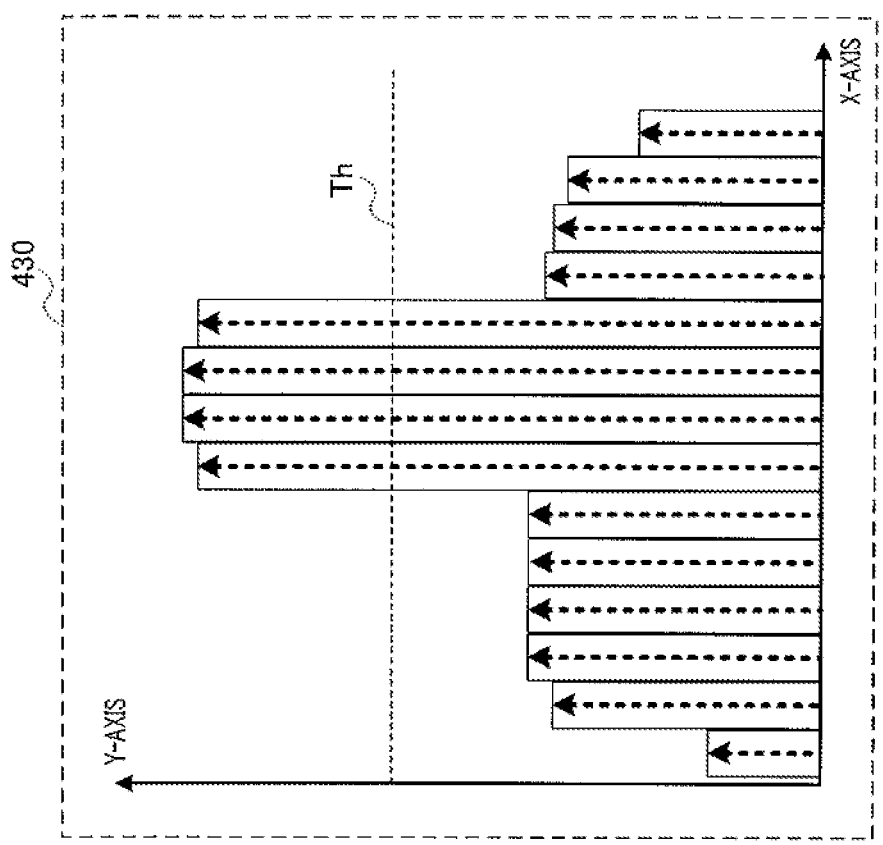
FIG. 17 is a diagram showing an example of a distance histogram with respect to Embodiment 3.

FIG. 17 is a diagram showing an example of a distance histogram generated by part region estimation section 131 based on omega region 422 shown in FIG. 15.

As shown in FIG. 17, in an X-Y coordinate system where the Y-axis represents perpendicular distance d(X), part region estimation section 131 generates distance histogram 430 representing a distribution of perpendicular distance d(X). Distance histogram 430 is so shaped that it rises in a shape corresponding to the shoulders, and at some point protrudes over a range corresponding to the center portion of the head.

By applying predetermined threshold Th, part region estimation section 131 performs thresholding on distance histogram 430 thus generated. Specifically, part region estimation section 131 replaces the Y-coordinates at the X-coordinates where perpendicular distance d(X) is equal to or greater than threshold Th with "1," and the Y-coordinates at the X-coordinates where perpendicular distance d(X) is less than threshold Th with "0." The value of threshold Th is so set that, in omega region 422, it would likely be greater than perpendicular distance d(X) of the upper ends of the shoulders, but less than perpendicular distance d(X) of the upper end of the head. The thresholding process is by no means limited to that above, and other methods may also be employed, one example being what is known as Otsu's thresholding (Otsu's method).

Figure 18:
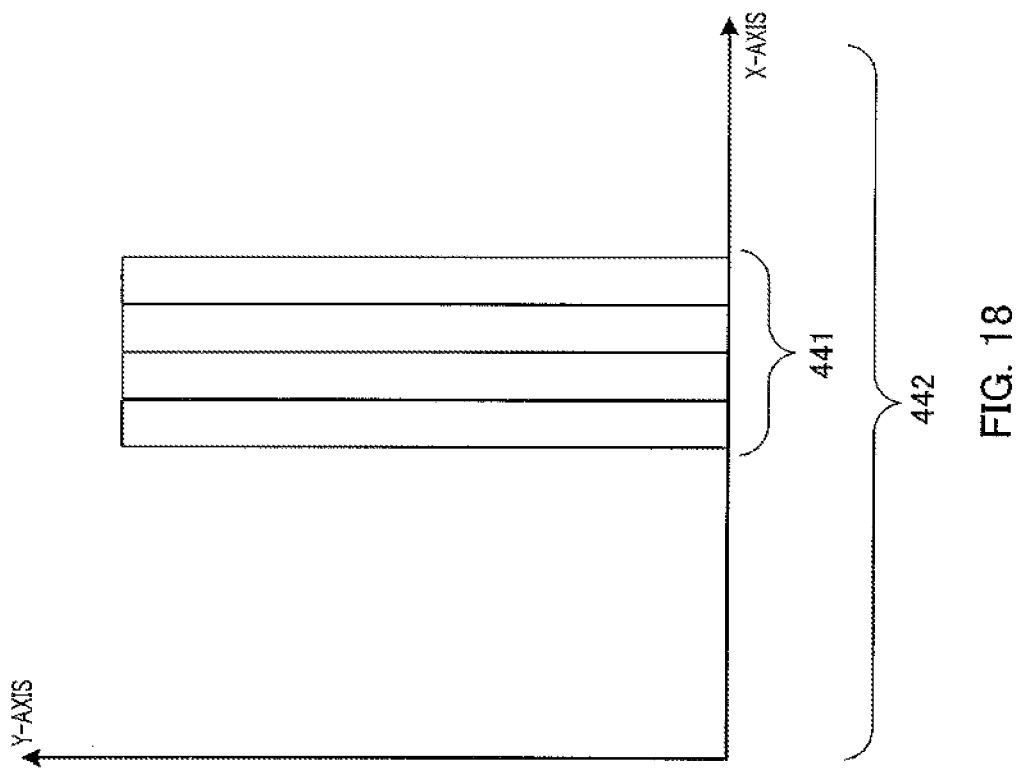
FIG. 18 is a diagram showing an example of a thresholded distance histogram with respect to Embodiment 3.

FIG. 18 is an example of results obtained by thresholding distance histogram 430 shown in FIG. 17.

As shown in FIG. 18, range 441 of value "1" indicates the range of X-coordinates of the image region of the center portion of the head (hereinafter referred to as "head region"). Overall range 442 containing range 441 of value "1" indicates the range of X-coordinates of the image region of the shoulders (hereinafter referred to as "shoulder region"). Accordingly, from image 420 of the image data, part region estimation section 131 extracts the X-axis direction range of omega region 422 as the X-axis direction range of the shoulder region, and the X-axis direction range of range 441 of value "1" as the X-axis direction range of the head region.

Based on the extracted shoulder region and head region, part region estimation section 131 computes various parameters indicating the positions and orientation of the reference parts.

Figure 19:
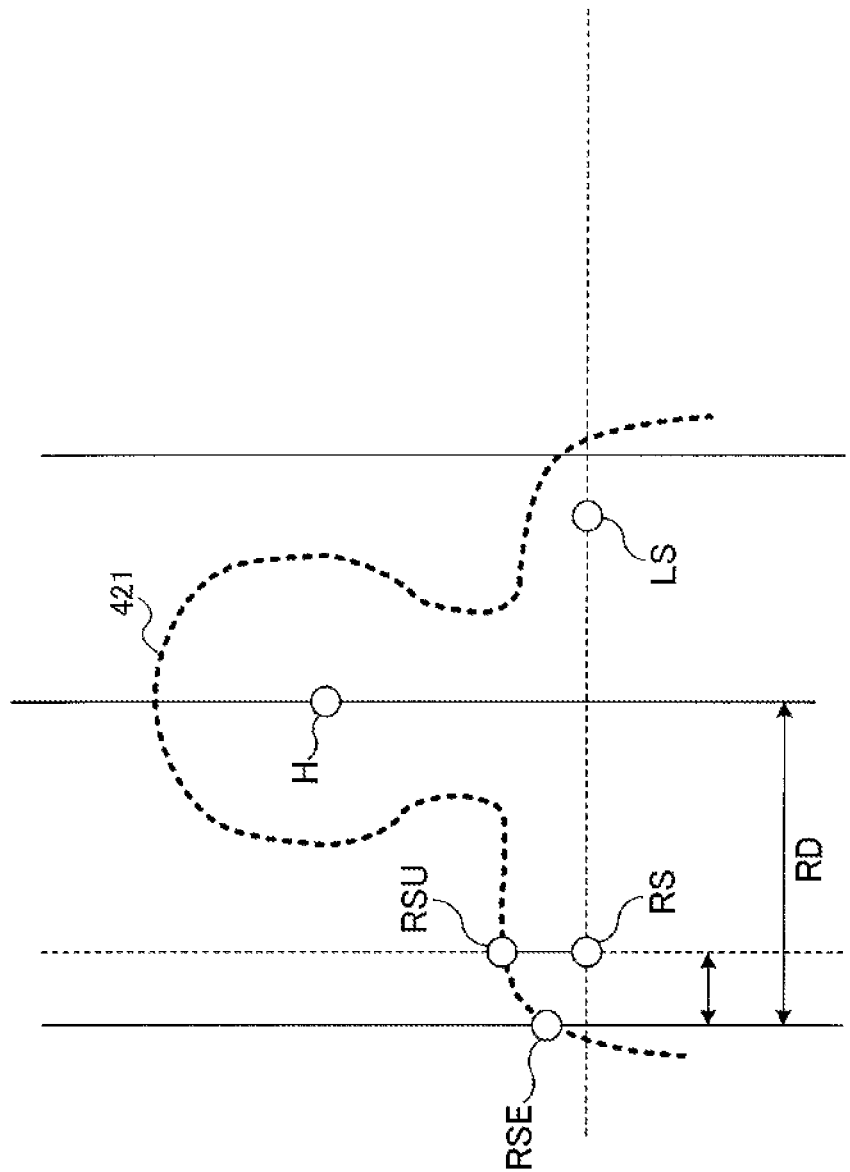
FIG. 19 is a diagram illustrating various parameters indicating reference parts with respect to Embodiment 3.

FIG. 19 is a diagram illustrating various parameters representing the reference parts.

As shown in FIG. 19, it is assumed that part region estimation section 131 uses H(xh, yh), RSE(x_rse), RD(x_rd), RS(x_rs, y_rs), RSU(y_rsu), and LS as symbols indicating the positions of the reference parts. The contents of the parentheses appended to the symbols indicate parameters for an X-Y coordinate system. H is the geometric center position of the head. RSE is the position of an end portion of the right shoulder. RD is the distance in the X-axis direction from the geometric center of the head to the end portion of the right shoulder. RS is the position of the right shoulder joint (hereinafter referred to as "right shoulder position"). RSU is the position of the apex of the right shoulder. LS is the position of the left shoulder joint (hereinafter referred to as "left shoulder position").

Part region estimation section 131 computes each parameter value as follows, for example.

First, based on whether or not (the torso of) the person is facing monocular camera 200, part region estimation section 131 determines the right shoulder region from among the shoulder region extracted based on the results of thresholding. Part region estimation section 131 determines whether or not the person is facing monocular camera 200 based on whether or not the skin colored components among the color information in the head region are at or above a predetermined threshold. For the case at hand, it is assumed that the person is facing monocular camera 200, and that the shoulder region on the left side of the image has been determined to be the right shoulder region.

Part region estimation section 131 next computes the geometric center position of the right shoulder region as right shoulder position RS(x_rs, y_rs). Part region estimation section 131 may also compute geometric center position H(xh, yh) of the head, and compute right shoulder position RS(x_rs, y_rs) using the distance between geometric center position H(xh, yh) and original omega shape 421 in the Y-axis direction (hereinafter referred to as "head height Δh"). Specifically, part region estimation section 131 may take a value, which is of a pre-defined ratio to head height Δh, as distance (xh−x_rs) from geometric center position H of the head to right shoulder position RS in the X-axis direction, for example. Part region estimation section 131 may also take a position that is lower than shoulder height by half the value of head height Δh, i.e., by Δh/2, to be the Y-coordinate of right shoulder position RS, i.e., y_rs, for example.

Furthermore, part region estimation section 131 computes, as position RSE(x_rse) of the end portion of the right shoulder, a point at which the edge gradient of omega shape 421 (i.e., the rate of change of the distance histogram) exceeds a threshold. Part region estimation section 131 computes distance RD(x_rd) in the X-axis direction between geometric center position H of the head and position RSE of the end portion of the right shoulder.

Finally, part region estimation section 131 estimates right shoulder position RS to be located at a position that is 80% of distance RD from geometric center position H of the head in the X-axis direction. Specifically, part region estimation section 131 computes X-coordinate x_rs of right shoulder position RS as x_rs=x_rse+0.2×RD. Part region estimation section 131 computes, as position RSU(y_rsu) of the apex of the right shoulder, the point of intersection between a straight perpendicular line that passes through right shoulder position RS (a straight line parallel to the Y-axis) and the edge of omega shape 421. Part region estimation section 131 computes Y-coordinate y_rs of right shoulder position RS as y_rs=y_rsu−0.2×RD.

Part region estimation section 131 carries out similar computations with respect to left shoulder position LS as well.

The computation methods for the various parameters are by no means limited to the examples provided above. By way of example, part lengths, such as shoulder width (e.g., the distance between right shoulder position RS and left shoulder position LS), might be stored in body constraint information storage section 110 as one form of body constraint information. In such cases, part region estimation section 131 may compute various parameters using that body constraint information.

This concludes this description of the first process of estimating the shoulder joint position of a person.

The second process of estimating the orientation of the torso of a person will now be described.

For the present embodiment, it is assumed that part region estimation section 131 performs the second process by referencing a reference part correspondence table pre-stored in body constraint information storage section 110 as one form of body constraint information.

The reference part correspondence table is a table that maps combinations of geometric center position H of the head, right shoulder position RS, and left shoulder position LS to the respective body orientations that can be estimated from the positions indicated by these combinations. In other words, the reference part correspondence table is a table that defines relative positional relationships of various parts. The combination of geometric center position H of the head, right shoulder position RS, and left shoulder position LS is hereinafter referred to as the "positions of the reference parts." The body orientation estimated from the positions of the reference parts is hereinafter referred to as the "orientation of the reference parts." The term "reference parts" refers to the omega-shaped portion indicating the head and shoulders of a person as discussed above. Accordingly, the orientation of the reference parts is the orientation of the body (torso) of a person.

Part region estimation section 131 derives from the reference part correspondence table the orientation of the reference parts corresponding to the positions of the reference parts computed based on the image data.

It is preferable that the positions of the reference parts included in the stored reference part correspondence table, as well as the positions of the reference parts computed by part region estimation section 131 based on the image data be normalized values independent of the size of the person on the screen. Specifically, part region estimation section 131 derives the orientation of the reference parts using values normalized in such a manner that, with geometric center position H of the head as the origin, the distance between geometric center position H of the head and right shoulder position RS or left shoulder position LS would be 1, for example.

The reference part correspondence table may also include right shoulder position RS and left shoulder position LS. The reference part correspondence table may also include the angle formed between a line passing through geometric center position H of the head and right shoulder position RS or left shoulder position LS and a straight perpendicular line passing through geometric center position H of the head (hereinafter referred to as "head perpendicular line"). The reference part correspondence table may also include the distance between geometric center position H of the head and left shoulder position LS relative to the distance between geometric center position H of the head and right shoulder position RS, where the latter distance is defined as being 1. Part region estimation section 131 derives the orientation of the reference parts by computing parameters corresponding to the parameters included in the reference part correspondence table.

FIG. 20 is a diagram showing example contents of a reference part correspondence table.

As shown in FIG. 20, reference part correspondence table 450 includes projection angle 452, coordinate 453 of left shoulder position LS, coordinates 454 of geometric center position H of the head, and reference part orientation 455, which are mapped to identifier 451. The various coordinates are expressed using a predetermined two-dimensional coordinate system parallel to the two-dimensional coordinate system of the screen, where right shoulder position RS is taken to be the origin, for example. Projection angle 452 is the angle of this predetermined two-dimensional coordinate system relative to the X-Z plane of three-dimensional coordinate system 410 described in connection with FIG. 4 (i.e., installation angle θ shown in FIG. 4), for example. Reference part orientation 455 is expressed as rotation angles relative to the X-, Y-, and Z-axes of three-dimensional coordinate system 410 described in connection with FIG. 4, for example. Each coordinate may also be expressed using a coordinate system that takes some other length to be 1, such as a part length of the arms, one's height, etc.

Part region estimation section 131 thus estimates the positions and orientation of the reference parts using body constraint information.

This concludes this description of the second process of estimating the orientation of the torso of a person, and thus of the reference part estimation process.

Next, in step S4300 in FIG. 14, part region estimation section 131 performs a process of estimating a part region for each part (hereinafter referred to as "part region estimation process") based on the estimated positions and orientation of the reference parts.

Example details of the part region estimation process will now be described.

For the present embodiment, it is assumed that part region estimation section 131 performs the part region estimation process by referencing a part region correspondence table pre-stored in body constraint information storage section 110 as one form of body constraint information.

The part region correspondence table is a table that maps the positions and orientation of the reference parts to part regions of other parts.

Part region estimation section 131 derives from the part region correspondence table a part region corresponding to the positions and orientation of the reference parts estimated from the image data.

Part regions may be defined in terms of pixel positions in the image of the image data, for example. Accordingly, with respect to all pixels in the entire image of the image data, part region estimation section 131 determines which part's part region each pixel belongs to.

FIG. 21 is a diagram showing example contents of a part region correspondence table.

As shown in FIG. 21, part region correspondence table 460 includes projection angle 462, head-shoulder region (reference parts) position 463, head-shoulder region (reference parts) orientation 464, and region 465 of each part, which are mapped to identifier 461.

Each position and region is represented by values of a two-dimensional coordinate system for the image, for example. Projection angle 462 is the angle of this predetermined two-dimensional coordinate system relative to the X-Z plane of three-dimensional coordinate system 410 described in connection with FIG. 4 (i.e., installation angle θ shown in FIG. 4), for example. Head-shoulder region position 463 is right shoulder position RS, for example. Head-shoulder region orientation 464 is expressed as rotation angles relative to the X-, Y-, and Z-axes of three-dimensional coordinate system 410 described in connection with FIG. 4, for example. Region 465 of each part is expressed in terms of the center coordinates and radius of a circle, assuming that the region can be approximated by a circle, for example. The radius is the part length.

If identifier 461 is the same as identifier 451 in reference part correspondence table 450, head-shoulder region orientation 464 does not necessarily have to be included in part region correspondence table 460.

In estimating part regions, other types of body constraint information may also be used. Furthermore, body constraint information may adopt configurations other than those discussed above.

Upon completion of part region estimation, part region estimation section 131 outputs as part region data to part candidate extraction section 132, with respect to all pixels of the entire image of the image data, information indicating whether or not each pixel is a part region for a part.

The part region data may have a structure where there is laid out, for example, pixel information Kij indicating, with respect to all pixel positions (i, j) in the image data, whether or not there is a corresponding part region of a part. Each element in pixel information Kij may, for example, assume a value of "1" if it belongs to a part region of a corresponding part, or "0" if not. For pixel information Kij, there are as many dimensions as there are parts, for example, as in Kij=[k1, k2]. In this case, k1 may correspond to the part region of the right upper arm, and k2 to the part region of the right forearm.

By way of example, if part region estimation section 131 determines that some pixel position Kab is included in the part region of the right upper arm but not in the part region of the right forearm, pixel information Kab=[1, 0] is generated. Part region estimation section 131 generates as part region data the thus generated set of pixel information for each pixel.

How part regions are to be represented by part region data is by no means limited to the example provided above. By way of example, part region data may indicate, for each part region pre-defined in the image, which part's part region it corresponds to, or it may indicate, for each part, the coordinates of the perimeter of the part region.

If normalized reference part positions are to be used in the reference part estimation process, it is preferable that the part region correspondence table include a part region corresponding to the normalized reference parts. As in the case of the reference part correspondence table discussed hereinabove, pert region data may also include other information such as right shoulder position RS, left shoulder position LS, and/or the like. Part region estimation section 131 derives the part region of each part by computing parameters corresponding to the parameters included in the part region correspondence table.

Figure 22:
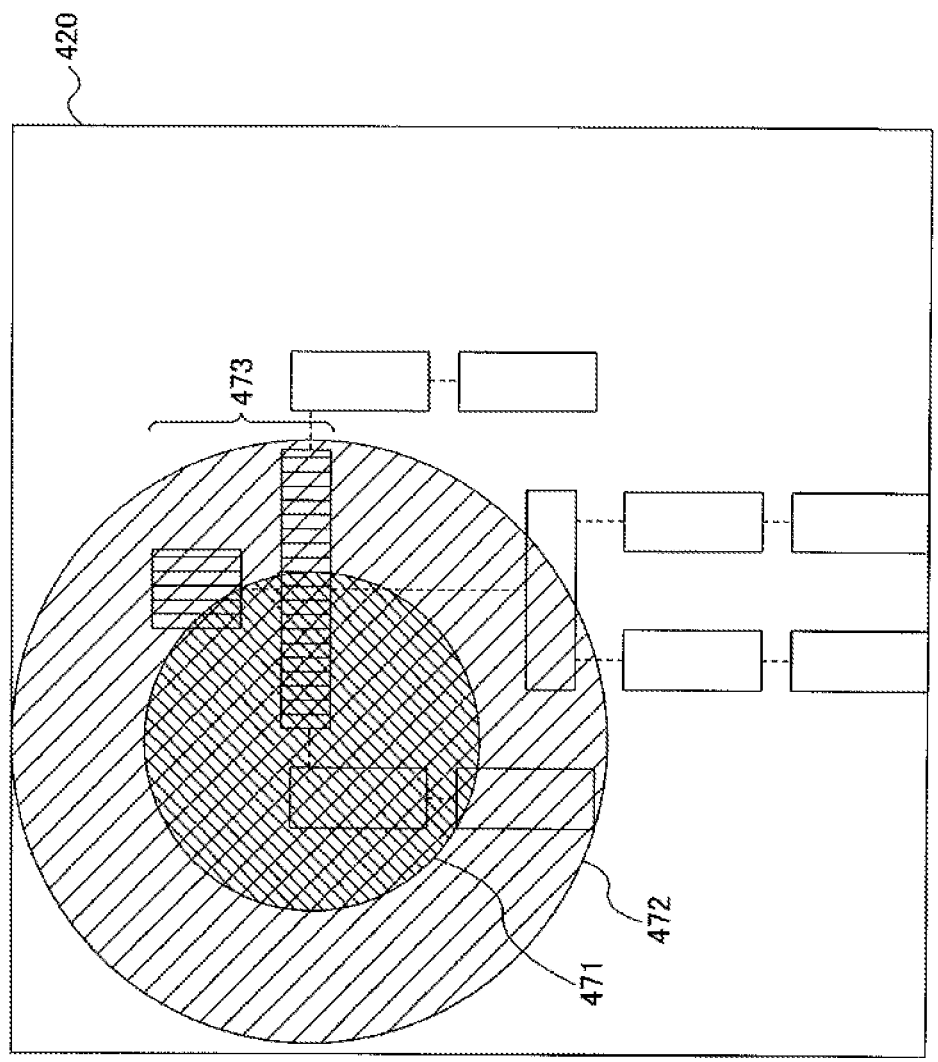
FIG. 22 is a diagram showing example contents of part region data with respect to Embodiment 3.

FIG. 22 is a diagram showing example contents of part region data. For purposes of convenience, the position of each part with respect to a case of an upright standing state is also shown in the drawing.

As shown in FIG. 22, the part region data indicates, with respect to image 420 of the image data, part region 471 of the right upper arm, and part region 472 of the right forearm. These part regions 471 and 472 are estimated with reference to the already estimated positions and orientation of reference parts 473 as mentioned above.

Part region estimation section 131 thus estimates the part region of each part using body constraint information.

This concludes this description of a part region estimation process.

Next, in step S4400 in FIG. 14, part candidate extraction section 132 extracts a part candidate with respect to the part region of each part, and generates part candidate information indicating the extracted part candidates.

A first example of the details of a process of generating an estimated likelihood map as part candidate information (hereinafter referred to as "estimated likelihood map generation process") will now be described.

Part candidate extraction section 132 first identifies, from the image data and for each pixel within the part region of each part, image features suited for representing the position and orientation states of the part, and computes a likelihood value indicating the likelihood that the part is located thereat. Part candidate extraction section 132 then generates an estimated likelihood map indicating a distribution of likelihood values for the pixels using the likelihood values computed from the image data. The likelihood values may be values normalized to fall within the range of 0 to 1, as well as real numbers including positive integers and negative numbers.

For the method of recognizing an object of interest within the image, one may employ a technique where a face is recognized as an object of interest within the image using a strong classifier that combines a plurality of weak classifiers, for example. This technique creates strong classifiers by combining the sums of a plurality of weak classifiers based on rectangular information through AdaBoost, combines the strong classifiers in a cascade, and recognizes an object of interest within the image. For the image features, scale-invariant feature transform (SIFT) features may be employed (e.g., see NPL 2 and NPL 3), for example. SIFT features are configured with 128-dimensional vectors, and are values that are computed for each pixel. Because SIFT features are unaffected by scale changes, rotation, or translation of the object to be detected, they are particularly effective for detecting parts that are rotatable in various directions, e.g., the arms. In other words, SIFT features are suited for the present embodiment which defines posture through the relative joint positions and angles of two or more parts.

When a method using SIFT features is applied to the present embodiment, strong classifiers Hk (where k=1, 2) are generated for each part region in advance through machine learning, and stored in part candidate extraction section 132, as in right upper arm (k=1), right forearm (k=2), and so forth. Classifiers Hk are generated by an AdaBoost algorithm. In other words, in generating strong classifiers Hk, learning is repeated until it is made possible to determine, with the desired level of accuracy, whether or not a plurality of training images prepared in advance for each part are the right upper arm, and whether or not they are the right forearm. Strong classifiers Hk are generated by connecting a plurality of weak classifiers in a cascade.

Upon computing an image feature for each part and each pixel, part candidate extraction section 132 inputs the image features to strong classifiers Hk. Part candidate extraction section 132 then computes the sum of values obtained by multiplying the output of each weak classifier forming the strong classifiers Hk with reliability a pre-obtained for each weak classifier. Part candidate extraction section 132 then subtracts predetermined threshold Th from the computed sum to compute likelihood value ck for each part and each pixel. For the present case, c1 represents a likelihood value for the right upper arm, and c2 a likelihood value for the right forearm.

Part candidate extraction section 132 expresses likelihood values Cij of the respective pixels, where the likelihood values of the respective parts are combined, as Cij=[c1, c2]. Part candidate extraction section 132 then outputs to posture estimation section 160 as an estimated likelihood map the likelihood values Cij of all the pixels in the entire image.

For each pixel, part candidate extraction section 132 may determine whether or not the pixel is included in any part region. If the pixel is included in some part region, part candidate extraction section 132 may compute a likelihood value using the classifier for that part, and if not, it may set the likelihood value for that part to 0. In other words, part candidate extraction section 132 may compute the products of determinant (Kij) of pixel information outputted from part region estimation section 131 and determinant (Cij) of likelihood values of the respective pixels computed irrespective of the part regions, and take the results thereof to be the final estimated likelihood map.

Figure 23:
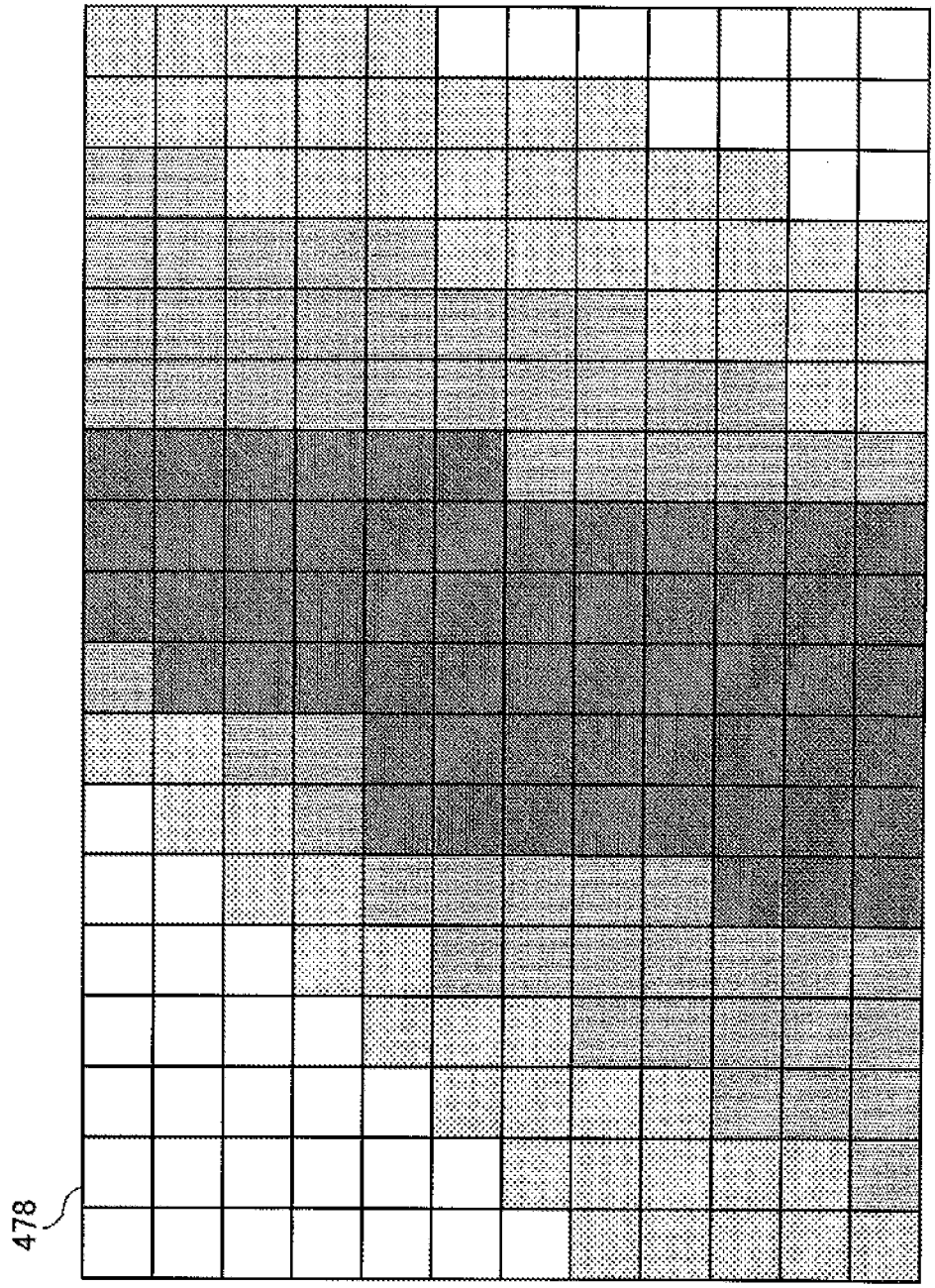
FIG. 23 is a diagram showing an example of an estimated likelihood map with respect to Embodiment 3.

FIG. 23 is a diagram showing an example of an estimated likelihood map. Here, the likelihood values of just one part (e.g., the right upper arm) in an estimated likelihood map are shown, where pixels with higher likelihood values are shown with darker shadings. As shown in FIG. 23, estimated likelihood map 478 represents a distribution of likelihoods regarding part presence.

With respect to the information for each pixel in the likelihood map, for example, the likelihood value for part k is denoted by ck, where, if there are n parts, the data structure would be such that likelihood vector Cij=[c1, c2 . . . , ck . . . , cn].

Part candidate extraction section 132 thus generates an estimated likelihood map.

This concludes this description of a first example of the details of an estimated likelihood map generation process.

A second example of the details of an estimated likelihood map generation process will now be described.

As in the technique disclosed in PL 1, for example, part candidate extraction section 132 generates an estimated likelihood map by extracting parallel lines from edges contained in the image data.

In this case, part candidate extraction section 132 extracts parallel lines by referencing a correspondence table that maps shoulder joint lengths to standard thickness values for various parts, the correspondence table being pre-stored in body constraint information storage section 110 as one form of body constraint information, for example. Part candidate extraction section 132 searches a part region for a pair of parallel lines spaced apart by a distance corresponding to the standard thickness for that part while rotating the direction of determination by 360°. Part candidate extraction section 132 repeats a process where, if there is a matching parallel line pair, a vote is cast for each pixel in the region enclosed by those parallel lines, and generates an estimated likelihood map based on the final number of votes for each pixel.

With such a method, the estimated likelihood map and the two-dimensional reference model map would include, for each pixel and each part, directions of parallel lines and numbers of votes (hereinafter referred to as "directional likelihood values"). By way of example, assuming that parallel line angles are divided into eight categories, the likelihood value of each pixel and each part would assume an eight-dimensional value corresponding to those eight directions. By way of example, further assuming that parallel line widths are divided into two categories, the likelihood value of each pixel and each part would assume a sixteen-dimensional (2×8=16) value. The parallel line distance or angle to be voted on may vary from part to part. By computing a plurality of parallel line widths and using the likelihood value of the width with the highest likelihood value, likelihood may be computed while absorbing differences in body type and clothing.

Part candidate extraction section 132 then determines, for each part, that the direction with the highest directional likelihood value is the main edge direction for that part, for example. In so doing, posture estimation section 160 may compute the sum of likelihood values for all pixels for each direction, and determine the direction with the highest sum to be the direction with the highest directional likelihood value.

Part candidate extraction section 132 thus generates an estimated likelihood map using body constraint information.

This concludes this description of a second example of the details of an estimated likelihood map generation process.

Next, in step S4500 in FIG. 14, posture estimation section 160 determines, based on part candidate information that has been appropriately complemented, whether or not the posture of the subject corresponds to any of a plurality of pre-set postures. These pre-set postures are, of weighted two-dimensional reference models, postures that have been set as references for determination.

Posture estimation section 160 makes this determination based on whether or not any of the weighted two-dimensional reference model maps match the estimated likelihood map. In this case, posture estimation section 160 performs a match level determination process in which, for example, it is determined whether or not a weighted two-dimensional reference model map and the estimated likelihood map match each other based on whether or not the level of match therebetween is of a predetermined level or greater.

An example of the details of a match level determination process will now be described. A first example of the details of a match level determination process corresponding to a case where the above-mentioned first example of the estimated likelihood map generation process is adopted will be described first.

Posture estimation section 160 first performs thresholding on the estimated likelihood map using a predetermined threshold. Specifically, posture estimation section 160 converts the likelihood value of each pixel and each part to a digital signal of "1" if it is equal to or greater than the predetermined threshold, or to a digital signal of "0" if it is less than the predetermined threshold.

Figure 24:
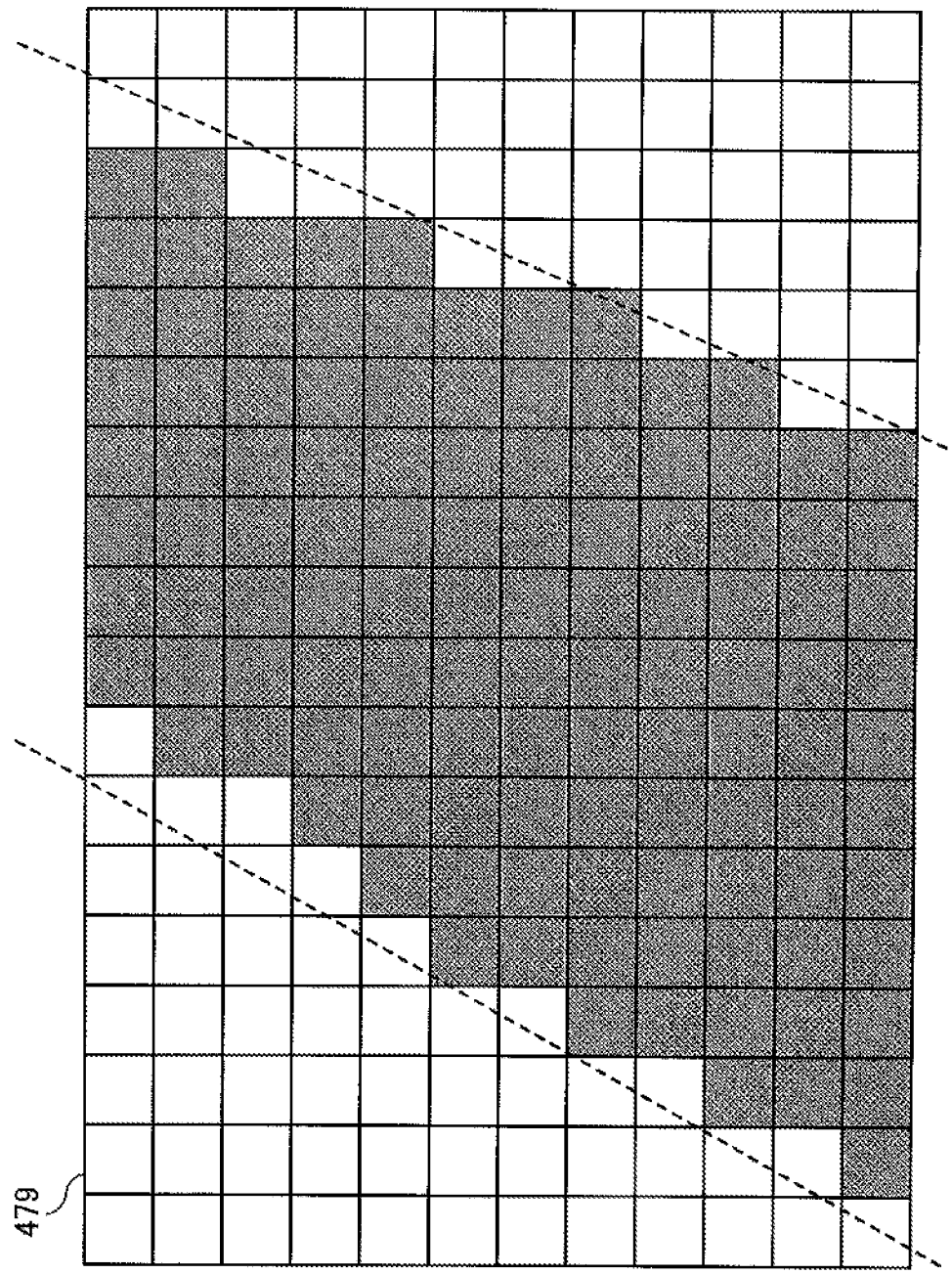
FIG. 24 is a diagram showing an example of a thresholded estimated likelihood map with respect to Embodiment 3.

FIG. 24 is a diagram showing an example of a post-thresholding state of the estimated likelihood map shown in FIG. 23. Here, pixels with a digital signal of "1" are shown in grey, and pixels with a digital signal of "0" in white. As shown in FIG. 24, thresholded estimated likelihood map 479 represents a distribution of portions where a part is likely located.

For each two-dimensional reference model map, posture estimation section 160 then computes the product of the thresholded likelihood values for each pixel between the estimated likelihood map and the weighted model map. Posture estimation section 160 further computes the products of weight values, and takes the sum of the values for all pixels and all parts to be an evaluation value. Specifically, posture estimation section 160 overlays the estimated likelihood map and the weighted model map on top of each other in a predetermined positional relationship, multiplies their thresholded likelihood value information and weight information with each other pixel by pixel, and computes the sum of the products for all pixels and parts.

Based on shoulder position information, posture estimation section 160 determines the positional relationship for overlaying the estimated likelihood map and the two-dimensional reference model map on top of each other. If the distances between both shoulders differ therebetween, overlaying may be carried out after the two-dimensional reference model map has been enlarged/reduced. Furthermore, posture estimation section 160 may shift the positional relationship through translation and rotation about the shoulder position, and perform the above-mentioned computation process for each positional relationship. Posture estimation section 160 may then obtain the largest value among the computed evaluation values and take it to be the final evaluation value representing the level of match with respect to the two-dimensional reference model map. Thus, even if there are errors in the shoulder position information of the estimated likelihood map, by finding the optimal overlay position, estimation accuracy may be improved. If there exists a two-dimensional reference model map for which this evaluation value is equal to or greater than a predetermined threshold, posture estimation section 160 determines that this two-dimensional reference model map and the estimated likelihood map are a match. The threshold is pro-set to an appropriate value through learning, and/or the like.

Posture estimation section 160 does not necessarily have to perform thresholding on the estimated likelihood map. In this case, posture estimation section 160 would be able to determine with greater precision the levels of match between the two-dimensional reference model maps and the estimated likelihood map. If thresholding is performed, however, posture estimation section 160 would be able to determine the level of match quickly.

Posture estimation section 160 thus determines the level of match between estimated likelihood maps and two-dimensional reference model maps.

This concludes this description of a first example of a match level determination process.

A second example of the details of a match level determination process corresponding to a case where the above-mentioned second example of an estimated likelihood map generation process is adopted will now be described.

For each part, posture estimation section 160 overlays the estimated likelihood map and a two-dimensional reference model map on top of each other in such a manner that key edge directions coincide therebetween, and computes the level of match. Subsequent processes are comparable to those in the above-mentioned first example.

A method that thus takes edge directions into account makes it possible to place constraints on the positional relationship for overlaying the estimated likelihood map and a two-dimensional reference model map on top of each other, thereby enabling a reduction in processing load.

This concludes this description of a second example of a match level determination process.

As a third example of an estimated likelihood map generation process, in computing the level of match between the estimated likelihood map and a two-dimensional reference model map, posture estimation section 160 may also use just the edge direction information.

A third example of an estimated likelihood map generation process will now be described.

By way of example, posture estimation section 160 takes the level of match with respect to angles formed between key edge directions of a plurality of specified parts to be an evaluation value representing the level of match between the estimated likelihood map and a two-dimensional reference model map. Specifically, for each specified part in the estimated likelihood map and in a weighted model map, the difference between angles formed between key edge directions is computed, the product of this difference and the weight of the corresponding part is computed, and the sum of all parts is taken to be an evaluation value. This evaluation value is such that a smaller value indicates a greater level of match. If the evaluation value falls within a predetermined range, posture estimation section 160 then determines that the posture of the subject is the posture corresponding to the two-dimensional reference model map in question.

An edge direction of a part corresponds to its axial direction. Accordingly, such posture estimation is comparable to estimating the direction of each part axis and the angle of each joint based on the image data, and evaluating, for the estimated part axis directions and joint angles, the levels of match with respect to reference models in various postures.

A method that thus determines level of match using edge directions alone renders unnecessary the process of determining an evaluation value by repeating computations on a per pixel basis, and is thus capable of further reducing the processing load. With respect to the weight values corresponding to the respective two-dimensional reference model maps, since an evaluation value can be computed simply with information regarding part identifiers and weight values, the weighting process can be made lighter, and the amount of weight value data reduced.

When the third example of an estimated likelihood map generation process is adopted, details of the match level determination process may be handled in a manner similar to the first example of a match level determination process.

This concludes this description of the third example of an estimated likelihood map generation process.

If some weighted model map matches the estimated likelihood map (S4500: YES), posture estimation section 160 proceeds to step S4600. If the weighted model maps do not match the estimated likelihood map (S4500: NO), posture estimation section 160 proceeds to step S4700.

In step S4600, posture estimation section 160 notifies the user, via information output apparatus 300, of the posture corresponding to the weighted model map that matches the estimated likelihood map, and proceeds to step S4700.

In step S4700, part region estimation section 131 determines whether or not there has been an instruction, through user operation and/or the like, to terminate processing. If there has not been any instruction to terminate processing (S4700: NO), part region estimation section 131 returns to step S4100, and proceeds to process the next still image. If there has been an instruction to terminate processing (S4700: YES), part region estimation section 131 terminates the sequence of processing.

Through such an operation, posture estimation apparatus 100 is able to perform posture estimation with the significance of the likelihoods of noisy parts (crowded areas) reduced, and the significance of the likelihoods of less noisy parts (dispersed areas) enhanced. Thus, posture estimation apparatus 100 is able to perform posture estimation that is robust against miniscule structural differences among people.

The inter-part minimum weight distance computation process in step S1000 in FIG. 7 and the weight range computation process in step S2000 may also be executed in reverse order.

As described above, for each posture, posture estimation apparatus 100 according to the present embodiment assigns a weight to each part in accordance with whether or not another part is located within the range indicated by its inter-part minimum weight distance. Posture estimation apparatus 100 is thus able to accurately discern crowded areas, which might contain a lot of noise, and dispersed areas, which characterize a posture, and perform posture estimation with the significance of crowded areas reduced, while the significance of dispersed areas is enhanced. Consequently, posture estimation apparatus 100 according to the present embodiment is able to accurately estimate the posture of a human having joints.

Weight computation section 150 may perform the weighting process pixel by pixel within each part, rather than by part.

Specifically, in this case, in the process of S3200 in FIG. 13, per-posture weight processing section 153 selects a pixel of interest instead of selecting a part of interest. Furthermore, in the process of step S3400, per-posture weight processing section 153 determines whether or not the pixel of interest is present within the range indicated by inter-part minimum weight distance Rpq corresponding to a combination of part p including the pixel of interest and comparison part q. If the pixel of interest is present (S3400: YES), per-posture weight processing section 153 proceeds to step S3500, and determines the weight for part p of the pixel of interest. On the other hand, if the pixel of interest is absent (S3400: NO), per-posture weight processing section 153 proceeds to step S3700, and determines the weight for part p of the pixel of interest. If the pixel of interest is included in a plurality of parts, per-posture weight processing section 153 makes determinations with respect to a plurality of inter-part minimum weight distances Rpq. Then, in the process of step S3800, per-posture weight processing section 153 determines whether or not all pixels have been processed.

Specifically, the per-pixel weight information for each posture includes map information including, for each pixel and each part, a flag, which assumes a value of "1" when included in that part or a value of "0" if not, and a weight corresponding to the part when included in that part. By thus computing a weight for each pixel and applying it to posture estimation, posture estimation apparatus 100 becomes able to perform posture estimation with even greater precision.

Weight computation section 150 may also use the position of the geometric center or part axis center of each part as the representative position for that part, determine, for example, whether another part is located within the inter-part minimum weight distance, and compute the weight of each part. This enables posture estimation apparatus 100 to expedite the weighting process, and is particularly suitable for the above-mentioned third example of an estimated likelihood map generation process.

Body candidate estimation section 130 may also estimate a silhouette, instead of a part candidate, as a body candidate. In this case, body candidate estimation section 130 extracts a silhouette based on background differences of color images using the method disclosed in NPL 1, for example. Body candidate estimation section 130 then outputs, as an estimated likelihood map, a map that expresses, through values of either "1" or "0", information indicating whether or not each pixel is included in the silhouette. However, in this case, the estimated likelihood map does not include part identification information.

For the present embodiment, the image data subject to person detection by posture estimation apparatus 100 has been described as being image data captured by monocular camera 200. However, this is by no means limiting. Furthermore, data of images captured by a stereo camera or a plurality of cameras may be used for person detection by posture estimation apparatus 100. When using image data of a stereo camera, posture estimation apparatus 100 may use image data captured by one of the cameras and position information of the subject as derived from the installation parameters of the stereo camera. Furthermore, when using image data of a plurality of cameras, posture estimation apparatus 100 may use image data captured by one of those cameras, and position information of the subject as derived from the installation parameters of each camera.

Furthermore, if the positions and orientation of the reference parts are known or specified, part region estimation section 131 need not perform the above-mentioned reference part estimation process. If, for example, the direction in which a person walks is fixed, and the orientation of the reference parts is generally uniform, part region estimation section 131 may hold body orientation information.

Furthermore, the part region estimation method performed by part region estimation section 131 is by no means limited to the examples provided above. By way of example, part region estimation section 131 may extract edge portions (hereinafter simply referred to as "edges") of an image from the image data, and estimate each part region based on the range of Y-coordinate values in the region enclosed by the edges. Specifically, for example, part region estimation section 131 may estimate, in the region enclosed by the edges, 20% of the region starting from the position where the Y-coordinate value is greatest to be a part region for the head. Similarly, for example, part region estimation section 131 may estimate the region from 15% to 65% to be a part region for the torso, the region from 55% to 85% to be a part region for the thighs, and the region from 75% to 100% to be a part region for the crura. In this case, values corresponding to the percentages of the various regions serve as body constraint information.

Furthermore, part region estimation section 131 may extract a moving body by computing background differences between images in the original video data, and take an entire region including the extracted region to be a part region candidate for each part. This expedites processing in estimating part regions.

Furthermore, posture estimation apparatus 100 may estimate the part region of each part of interest by repeating a process where part positions are estimated one by one in order of increasing distance from the reference parts, and where the part region of the next part is estimated based on the estimated position.

Furthermore, posture estimation apparatus 100 does not necessarily have to perform part region estimation. In this case, part candidate extraction section 132 would compute likelihood values uniformly for all regions in the image.

For the present embodiment, weight computation section 150 determined bi-level weights. However, it may also determine weights of three levels or more (hereinafter referred to as "multi-level").

An example of a method of determining multi-level weights will now be described.

A first method of determining multi-level weights will first be described. This first method is an example where the distribution of weights is varied in relation to the inter-part maximum distance (the level of spread of the body) which varies from posture to posture.

For each part, per-posture weight processing section 153 computes in advance maximum value R'p for the distance relative to another part (i.e., the distance between part of interest p and comparison part q) with respect to a movement that satisfies the body constraint information.

For each posture and for each combination of part of interest p and comparison part q, per-posture weight processing section 153 computes weight Wpq using Equation (4) below, for example, where R"pq is the distance to another part (i.e., the distance between part of interest p and comparison part q) in that posture.

$$Wpq=(Wmax-Wmin) \times (R"pq-Rpq)/(R'p-Rpq)+Wmin \quad \text{(Equation 4)}$$

In Equation (4), if R"pq=R'p, then Wpq=Wmax. For each posture and each part of interest p, per-posture weight processing section 153 determines the smallest of computed weights Wpq to be the final weight.

A second method of determining multi-level weights will now be described. This second method is an example where, instead of computing maximum value R'p for the distance to another part, weights are set in multiple levels in accordance with pre-defined constants. A description is provided below with regard to an example where tri-level weights are set.

For each posture and each part of interest p, per-posture weight processing section 153 first determines whether or not there exists any comparison part q for which distance R"pq is equal to or less than its inter-part minimum weight distance Rpq. If any such comparison part q exists, per-posture weight processing section 153 determines minimum weight Wmin as the weight of part of interest p in that posture.

For each posture and with respect to part of interest p whose weight is undetermined, per-posture weight processing section 153 next determines whether or not there exists any comparison part q for which distance R"pq is equal to or less than a predetermined value, the predetermined value being a multiple (by a constant factor) of inter-part minimum weight distance Rpq between that part of interest p and comparison part q. If the constant factor is 0.5, this predetermined value would be Rpq×2. In this case, it is determined whether or not R"pq×0.5≤Rpq. If any such comparison part q exists, per-posture weight processing section 153 determines, as the weight of part of interest p in that posture, a value that is a multiple (by a constant factor) of the difference between minimum weight Wmin and maximum weight Wmax. If the constant factor is 0.5, this value would be (Wmax−Wmin)×0.5+Wmin.

Finally, for each posture and with respect to part of interest p whose weight is undetermined, per-posture weight processing section 153 determines maximum weight Wmax to be its weight. This part of interest p is a part with respect to which there exists no comparison part q for which distance R"pq is equal to or less than a predetermined value, the predetermined value being a multiple (by a constant factor) of inter-part minimum weight distance Rpq between that part of interest p and comparison part q.

By performing such multi-level weighting, posture estimation apparatus 100 is able to adjust the extent to which each part affects estimation accuracy in such a manner as to closely reflect the degree of crowdedness. It is thus able to attain better accuracy for posture estimation.

Figure 25:
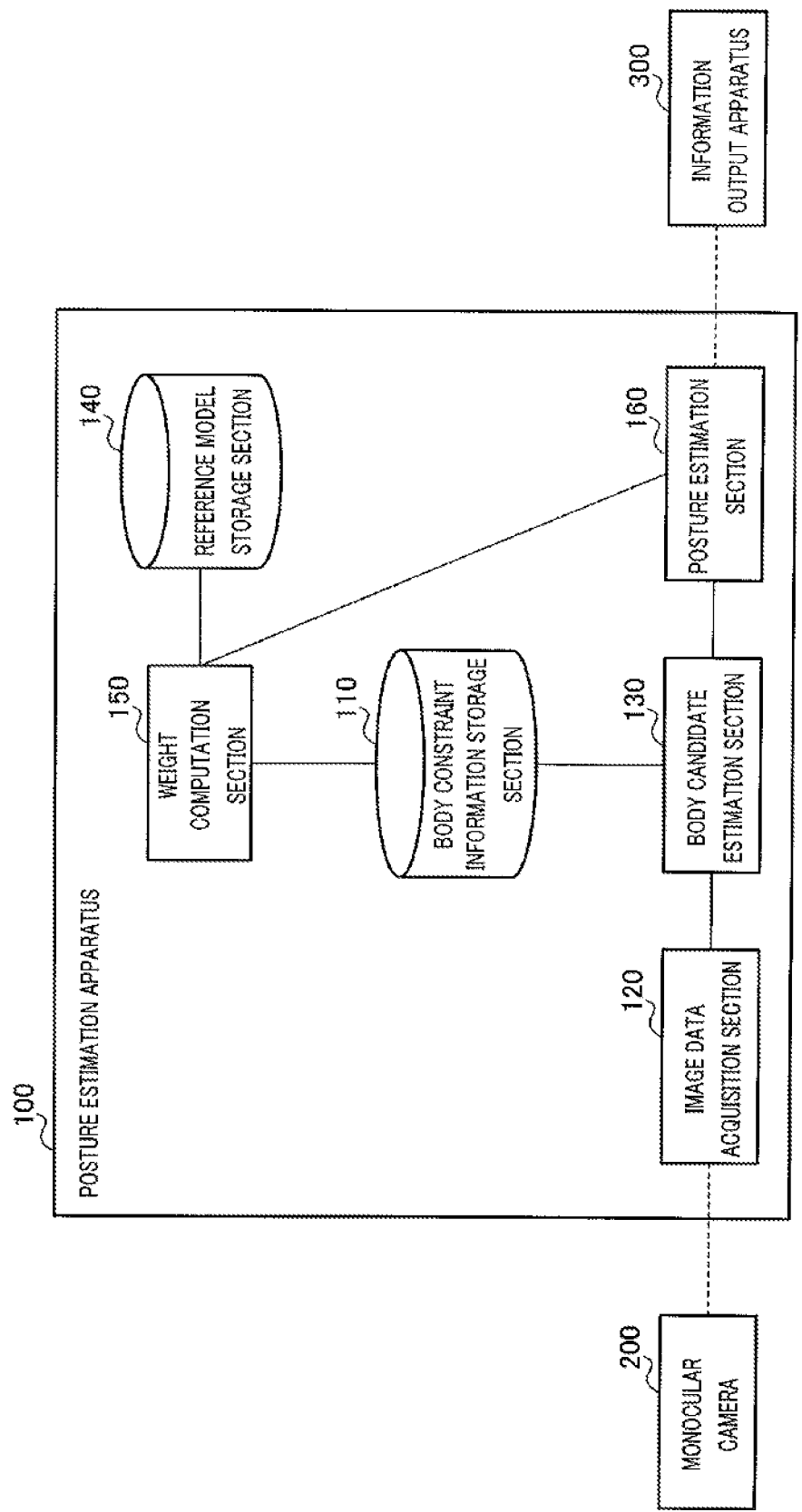
FIG. 25 is a block diagram showing a second configuration example of a posture estimation apparatus according to Embodiment 3.

For the present embodiment, descriptions have been provided where reference models (two-dimensional reference model maps) are obtained by posture estimation section 160 directly from reference model storage section 140. However, this is by no means limiting. By way of example, with a configuration such as that shown in FIG. 25, posture estimation section 160 may obtain reference models via weight computation section 150. In this case, weight computation section 150 may, for example, compute weights as it receives requests from posture estimation section 160, and output weight information along with the reference models obtained in the process. Weight computation section 150 may also change the various values in a two-dimensional reference model map to values that reflect the weights, and output the two-dimensional reference model map thus changed.

For the present embodiment, weight computation section 150 and posture estimation section 160 have been described as being disposed in the same apparatus. However, this is by no means limiting. Weight computation section 150 may be disposed in an apparatus separate from that of posture estimation section 160, for example.

Figure 26:
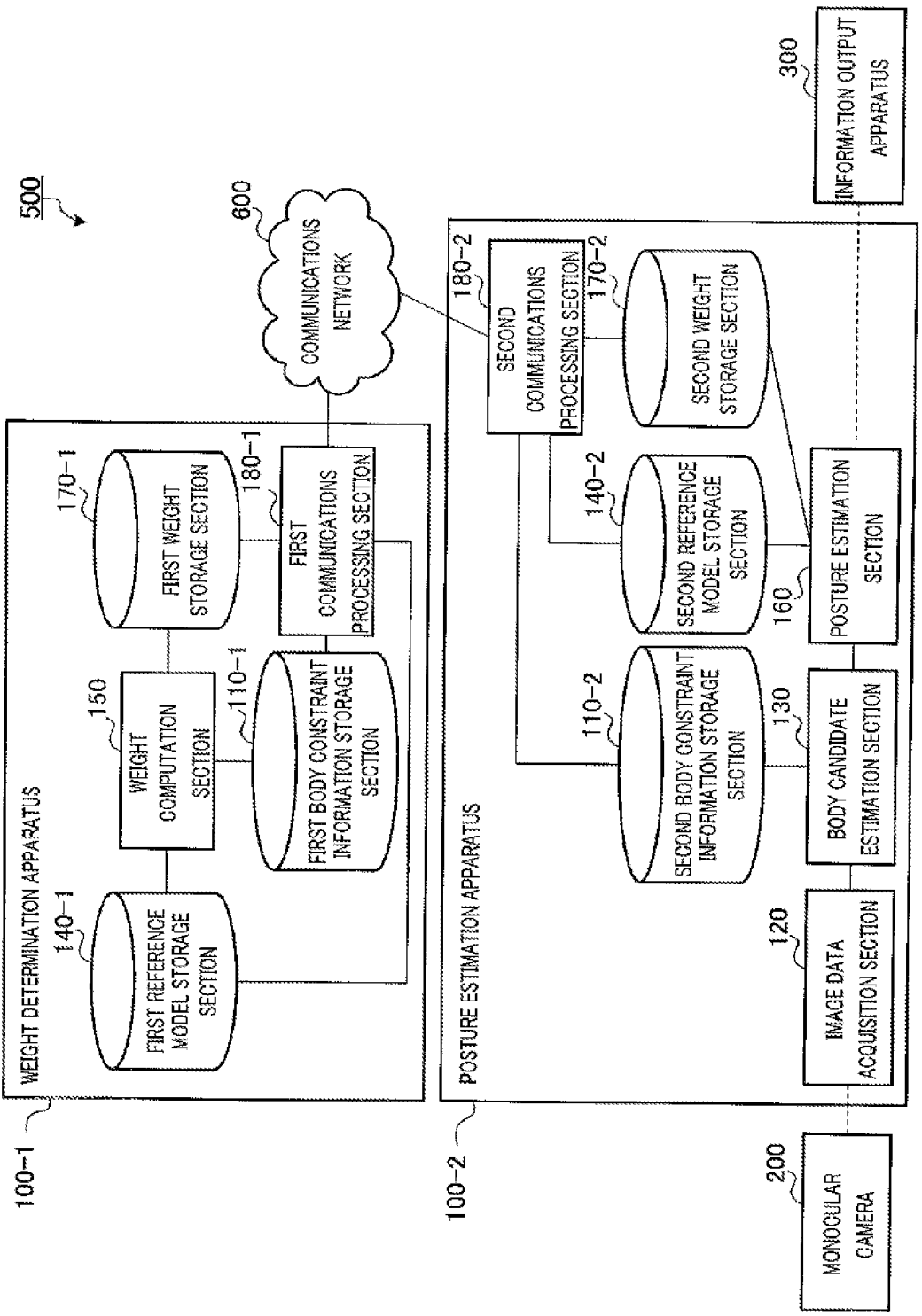
FIG. 26 is a block diagram showing a third configuration example of a posture estimation apparatus according to Embodiment 3.

FIG. 26 is a block diagram showing a configuration of a posture estimation system where weight computation section 150 and posture estimation section 160 are disposed in separate apparatuses.

As shown in FIG. 26, posture estimation system 500 includes weight determination apparatus 100-1, and posture estimation apparatus 100-2. Weight determination apparatus 100-1 performs processes up to the determination of weights. Posture estimation apparatus 100-2 performs a posture estimation process applying those weights.

Weight determination apparatus 100-1 includes: first body constraint information storage section 110-1; first reference model storage section 140-1; weight computation section 150; first weight storage section 170-1; and first communications processing section 180-1. Posture estimation apparatus 100-2 includes: second body constraint information storage section 110-2; second reference model storage section 140-2; second weight storage section 170-2; image data acquisition section 120; body candidate estimation section 130; posture estimation section 160; and second communications processing section 180-2.

First communications processing section 180-1 and second communications processing section 180-2 are communicably connected to each other via communications network 600, e.g., the Internet.

First body constraint information storage section 110-1 and first reference model storage section 140-1 correspond to body constraint information storage section 110 and reference model storage section 140 in FIG. 3, respectively. First weight storage section (weight information storage section) 170-1 stores weight information which indicates the weights determined by weight computation section 150. First body constraint information storage section 110-1, first reference model storage section 140-1, and first weight storage section 170-1 are each connected to first communications processing section 180-1.

Through its communications with first communications processing section 180-1, second communications processing section 180-2 (weight information acquisition section) obtains the respective information stored in first body constraint information storage section 110-1, first reference model storage section 140-1, and first weight storage section 170-1. Second communications processing section 180-2 then stores the obtained body constraint information, reference models, and weight information in second body constraint information storage section 110-2, second reference model storage section 140-2, and second weight storage section 170-2, respectively. In other words, body constraint information, reference models, and weight information are commonly stored on weight determination apparatus 100-1 and posture estimation apparatus 100-2.

Body candidate estimation section 130 performs processing by referencing second body constraint information storage section 110-2. Posture estimation section 160 performs processing by referencing second reference model storage section 140-2 and second weight storage section 170-2.

This posture estimation system 500, too, is able to perform posture estimation with the significance of crowded areas, which are prone to noise, reduced, and to accurately estimate the posture of a human having joints.

By thus separating apparatuses, it is made possible to simplify the configuration of the apparatus that performs posture estimation, while also achieving accurate posture estimation. Furthermore, since the weight information and other information that have been computed can be shared among a plurality of apparatuses in performing posture estimation, convenience is improved for cases where the posture estimation process is to be performed in a plurality of locations, and the cost of the system as a whole can also be reduced.

The transfer of information from weight determination apparatus 100-1 to posture estimation apparatus 100-2 may be performed by means of a recording medium on which the information is stored instead of via communications. In this case, weight determination apparatus 100-1 and posture estimation apparatus 100-2 will need an interface for recording and reading information on and from recording media. On the other hand, in this case, weight determination apparatus 100-1 and posture estimation apparatus 100-2 need not necessarily include first communications processing section 180-1 and second communications processing section 180-2.

Although the various embodiments above have been described in connection with their application in human posture estimation, the claimed invention is by no means limited as such, and may also be applied to posture estimation for various objects, besides humans, having a plurality of parts articulated by one or more joints (e.g., robots).

The disclosure of the specification, drawings, and abstract included in Japanese Patent Application No. 2011-45012 filed on Mar. 2, 2011, is incorporated herein by reference in its entirety.

INDUSTRIAL APPLICABILITY

The claimed invention is useful for posture estimation apparatuses, posture estimation systems, and posture estimation methods capable of accurately estimating the posture of an object having one or more joints, e.g., a human.

REFERENCE SIGNS LIST

100 Posture estimation apparatus
100-1 Weight determination apparatus
100-2 Posture estimation apparatus
110 Body constraint information storage section
110-1 First body constraint information storage section
110-2 Second body constraint information storage section
120 Image data acquisition section
130 Body candidate estimation section
131 Part region estimation section
132 Part candidate extraction section
140 Reference model storage section
140-1 First reference model storage section
140-2 Second reference model storage section
150 Weight computation section
151 Inter-part minimum weight distance computation section
152 Maximum-minimum weight computation section
153 Per-posture weight processing section
160 Posture estimation section
170-1 First weight storage section
170-2 Second weight storage section
180-1 First communications processing section
180-2 Second communications processing section
200 Monocular camera
300 Information output apparatus
500 Posture estimation system
600 Communications network

The invention claimed is:

1. A posture estimation apparatus that estimates the posture of an object, the posture estimation apparatus comprising a processor, executing instructions stored in a memory, configured to:
   obtain image data from images of the object continuously taken with a camera;
   estimate, based on the image data, a reference part and a plurality of parts articulated by one or more joints;
   store, on a per posture basis, a reference model defining relative positions of the plurality of parts with respect to the reference part;
   estimate a crowded area crowded with any of the reference part and the plurality of parts on a per posture basis and assign, on a per posture basis, respective weights to the plurality of parts based on the estimated crowded area, the weights for the parts located in the crowded area being lesser than the weight for other parts in the same posture;
   estimate relative positions of the plurality of parts of the object with respect to the reference part of the object from the image data;
   estimate the posture of the object by calculating a level of match between the relative positions defined by the reference model and the relative positions of the object while using the weights;

compute, on a per part basis, an inter-part minimum weight distance indicating a range where, when another part is located thereat, a presence of the other part becomes noise with respect to estimation, based on a part thickness of the part;

hold a weight range;

for each posture and within the weight range, determine the weights, the weight for a part among the parts of the reference model with respect to which the other part corresponding to the inter-part minimum weight distance of the part is located within a range indicated by the inter-part minimum weight distance being lesser than the weight for a part among the parts of the reference model with respect to which the other part corresponding to the inter-part minimum weight distance of the part is not located within a range indicated by the inter-part minimum weight distance; and determine the weight range based on a number of parts subject to the estimated posture of the object.

2. The posture estimation apparatus according to claim 1, wherein the processor is further configured to compute, on a per part basis, the inter-part minimum weight distance based on an angle error of the part that is to be ignored with respect to posture estimation.

3. The posture estimation apparatus according to claim 2, wherein the processor is further configured to determine, on a per posture and per part basis, the weight for the part based on a minimum value of the distance to another part.

4. The posture estimation apparatus according to claim 3, wherein the processor is further configured to store body constraint information comprising the part thickness and the angle error, the body constraint information being a constraint condition regarding a body type and posture of the object, wherein the part thickness and the angle error are obtained from the stored body constraint information.

5. The posture estimation apparatus according to claim 4, wherein the object comprises a human.

6. A posture estimation system comprising:

a posture estimation apparatus that estimates the posture of an object including a reference part and a plurality of parts articulated by one or more joints based on image data that images the object, said image data being obtained from images of the object continuously taken with a camera and said reference part and a plurality of parts being estimated based on the image data; and a weight determination apparatus comprising a processor, executing instructions stored in a memory, configured to:

store, on a per posture basis, a reference model defining relative positions of the plurality of parts with respect to the reference part;

estimate a crowded area crowded with any of the reference part and the plurality of parts on a per posture basis and assign, on a per posture basis, respective weights to the plurality of parts based on the estimated crowded area, the weights for the parts located in the crowded area being lesser than the weight for other parts in the same posture; and store weight information indicating the weights, wherein the posture estimation apparatus comprises a processor, executing instructions stored in a memory, configured to:

store the reference model;

obtain the weight information from the weight determination apparatus;

estimate relative positions of the plurality of parts of the object with respect to the reference part of the object from the image data;

estimate the posture of the object by calculating a level of match between the relative positions defined by the reference model and the relative positions of the object while using the obtained weight information;

compute, on a per part basis, an inter-part minimum weight distance indicating a range where, when another part is located thereat, a presence of the other part becomes noise with respect to estimation, based on a part thickness of the part;

hold a weight range;

for each posture and within the weight range, determine the weights, the weight for a part among the parts of the reference model with respect to which the other part corresponding to the inter-part minimum weight distance of the part is located within a range indicated by the inter-part minimum weight distance being lesser than the weight for a part among the parts of the reference model with respect to which the other part corresponding to the inter-part minimum weight distance of the part is not located within a range indicated by the inter-part minimum weight distance; and determine the weight range based on a number of parts subject to the estimated posture of the object.

7. A posture estimation method that estimates the posture of an object, the posture estimation method comprising the steps of:

obtaining, by a processor, image data from images of the object continuously taken with a camera;

estimating, by the processor, a reference part and a plurality of parts articulated by one or more joints based on the image data;

using, by the processor, a reference model that defines relative positions of the plurality of parts with respect to the reference part on a per posture basis;

estimating, by the processor, a crowded area crowded with any of the reference part and the plurality of parts on a per posture basis;

assigning, by the processor, on a per posture basis, respective weights to the plurality of parts based on the estimated crowded area, the weights for the parts located in the crowded area being lesser than the weight for other parts in the same posture;

estimating, by the processor, relative positions of the plurality of parts of the object with respect to the reference part of the object from the image data;

estimating, by the processor, the posture of the object by calculating a level of match between the relative positions defined by the reference model and the relative positions of the object while using the weights;

compute, by the processor, on a per part basis, an inter-part minimum weight distance indicating a range where, when another part is located thereat, a presence of the other part becomes noise with respect to estimation, based on a part thickness of the part;

hold, by the processor, a weight range;

for each posture and within the weight range, determine, by the processor, the weights, the weight for a part among the parts of the reference model with respect to which the other part corresponding to the inter-part minimum weight distance of the part is located within a range indicated by the inter-part minimum weight distance being lesser than the weight for a part among the parts of the reference model with respect to which the other part corresponding to the inter-part minimum weight distance of the part is not located within a range indicated by the inter-part minimum weight distance; and determine, by the processor, the weight range based on a number of parts subject to the estimated posture of the object.

* * * * *